US012678078B2

(12) United States Patent (10) Patent No.: US 12,678,078 B2
Masciotti et al. (45) Date of Patent: Jul. 14, 2026

(54) INTERFERENT DETECTION IN AN ANALYTE MONITORING SYSTEM

(71) Applicant: Senseonics, Incorporated, Germantown, MD (US)

(72) Inventors: James Masciotti, Germantown, MD (US); Andrew DeHennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 1280 days.

(21) Appl. No.: 17/097,983

(22) Filed: Nov. 13, 2020

(65) Prior Publication Data

US 2021/0137420 A1 May 13, 2021

Related U.S. Application Data

(60) Provisional application No. 62/934,589, filed on Nov. 13, 2019.

(51) Int. Cl.
 *A61B 5/1459* (2006.01)
 *A61B 5/00* (2006.01)
  (Continued)

(52) U.S. Cl.
 CPC ............ *A61B 5/1459* (2013.01); *A61B 5/002* (2013.01); *A61B 5/1451* (2013.01);
  (Continued)

(58) Field of Classification Search
 CPC . A61B 5/1459; A61B 5/1451; A61B 5/14532;
  A61B 5/1455
 See application file for complete search history.

(56) References Cited

U.S. PATENT DOCUMENTS 6,330,464 B1 * 12/2001 Colvin, Jr. ........... A61B 5/1459
  128/903
8,216,138 B1 7/2012 McGarraugh
  (Continued)

FOREIGN PATENT DOCUMENTS

CN 106535762 A 3/2017
CN 107847170 A 3/2018
  (Continued)

OTHER PUBLICATIONS

Romo-Cardenas et al. (Insulin overlapping in whole blood FTIR spectroscopy in blood glucose measurements) (Year: 2017).*

*Primary Examiner* — Christian Jang
(74) *Attorney, Agent, or Firm* — Rothwell, Figg, Ernst & Manbeck, P.C.

(57) ABSTRACT

Analyte monitoring methods and systems for interferent detection. The methods may include using one or more analyte detectors of an analyte sensor to generate one or more analyte measurements indicative of an analyte level in a first medium. The methods may include using one or more interferent detectors of the analyte sensor and/or one or more interferent sensors of a transceiver to generate one or more interferent measurements indicative of an interferent level in the first medium. The methods may include using a transceiver interface of the analyte sensor to convey the one or more analyte measurements and using a sensor interface of the transceiver to receive the one or more analyte measurements from the analyte sensor. The methods may include using the transceiver to calculate an analyte level in a second medium using at least the one or more analyte measurements and the one or more interferent measurements.

20 Claims, 21 Drawing Sheets

(51) Int. Cl.
     A61B 5/145      (2006.01)
     A61B 5/1473     (2006.01)
     A61B 5/1486     (2006.01)

(52) U.S. Cl.
     CPC ........ A61B 5/14532 (2013.01); A61B 5/1473
                (2013.01); A61B 5/14865 (2013.01)

(56)                  References Cited

U.S. PATENT DOCUMENTS

| | | | |
|---|---|---|---|
| 10,912,498 B2* | 2/2021 | Emken | A61B 5/1451 |
| 2005/0161346 A1 | 7/2005 | Simpson et al. | |
| 2006/0197015 A1 | 9/2006 | Sterling et al. | |
| 2008/0112853 A1* | 5/2008 | Hall | G01N 21/3577 |
| | | | 422/68.1 |
| 2009/0043171 A1 | 2/2009 | Rule | |
| 2012/0283538 A1 | 11/2012 | Rose et al. | |
| 2013/0006069 A1 | 1/2013 | Gil et al. | |
| 2013/0344619 A1 | 12/2013 | Crane et al. | |
| 2016/0345873 A1 | 12/2016 | Patel et al. | |
| 2017/0156647 A1 | 6/2017 | Schmelzeisen-Redeker et al. | |
| 2017/0191955 A1 | 7/2017 | Zou et al. | |
| 2018/0279923 A1* | 10/2018 | Chen | A61B 5/14556 |
| 2018/0303387 A1 | 10/2018 | Dehennis et al. | |
| 2018/0360355 A1 | 12/2018 | Chavan et al. | |
| 2019/0090790 A1 | 3/2019 | Chen et al. | |
| 2019/0094232 A1 | 3/2019 | Chen et al. | |

FOREIGN PATENT DOCUMENTS

| | | | |
|---|---|---|---|
| WO | 2016/137444 A1 | 9/2016 | |
| WO | 2019/118060 A1 | 6/2019 | |

* cited by examiner

50

Sensor
(subcutaneous)
100

13.56 MHz

Power &
Data

Transceiver
101

Bluetooth Low
Energy

Smartphone
with Mobile
Medical App
107

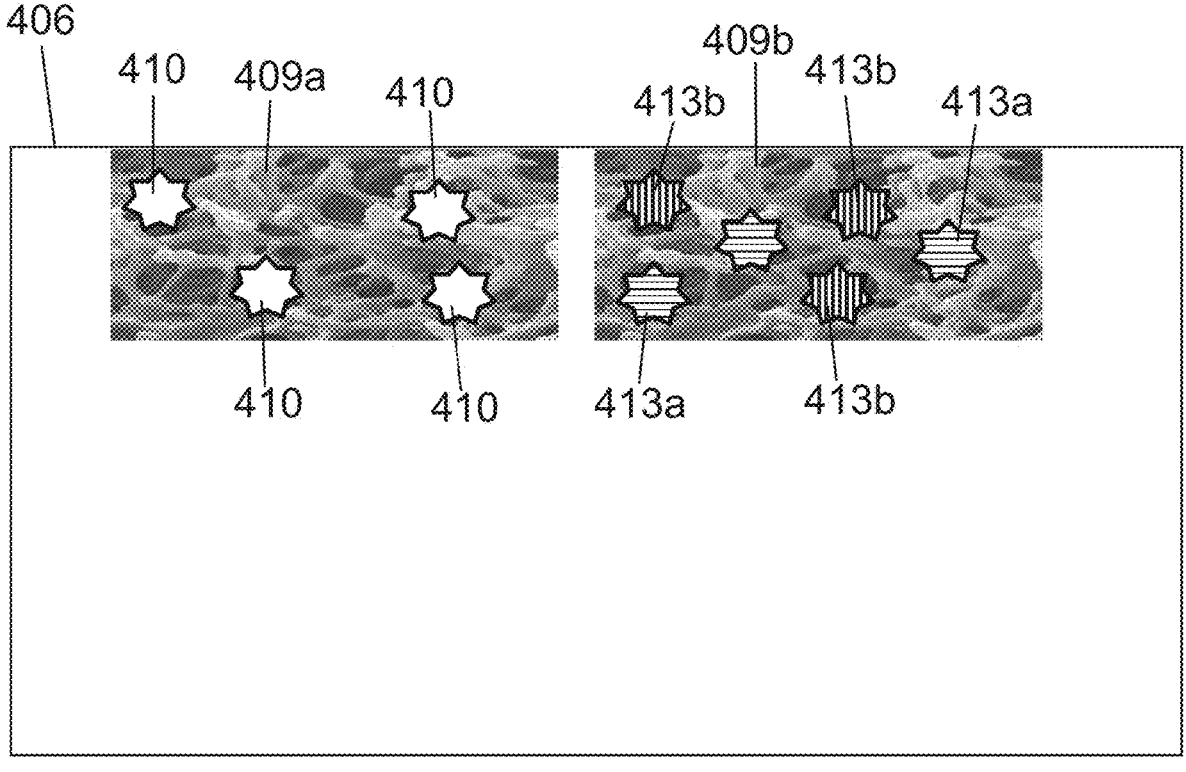
FIG. 7H
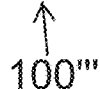
100""

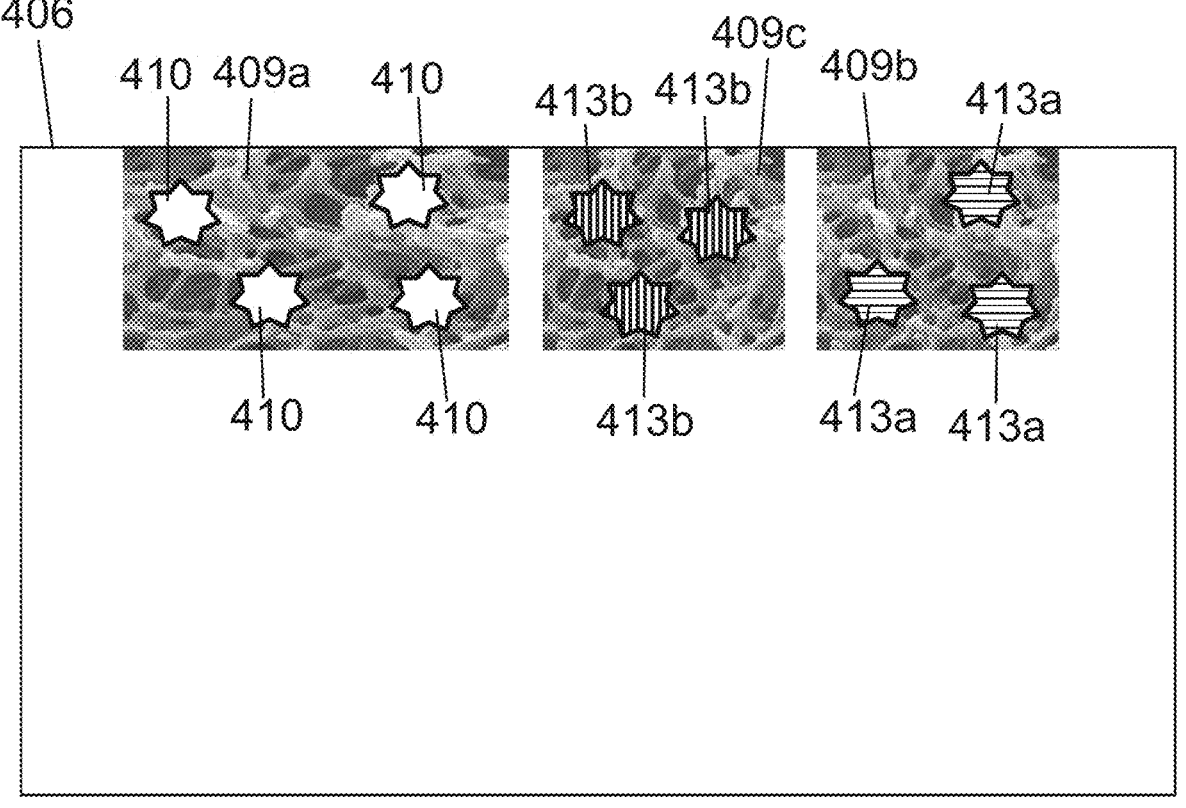
FIG. 7I
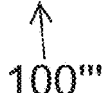
100""

INTERFERENT DETECTION IN AN ANALYTE MONITORING SYSTEM

CROSS-REFERENCE TO RELATED APPLICATION

The present application claims the benefit of priority to U.S. Provisional Application Ser. No. 62/934,589, filed on Nov. 13, 2019, which is incorporated herein by reference in its entirety.

BACKGROUND

Field of Invention

Aspects of the present invention relate to systems and methods for analyte monitoring. Specifically, aspects of the present invention may relate to interferent detection in an analyte monitoring system.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations.

SUMMARY

One aspect of the invention may provide an analyte monitoring system including an analyte sensor and a transceiver. The analyte sensor may include one or more analyte detectors configured to generate one or more analyte measurements indicative of an analyte level in a first medium.

The analyte sensor may include one or more interferent detectors configured to generate one or more interferent measurements indicative of an interferent level in the first medium. The analyte sensor may include a transceiver interface configured to convey the one or more analyte measurements and the one or more interferent measurements. The transceiver may include a sensor interface configured to receive the one or more analyte measurements and the one or more interferent measurements from the analyte sensor. The transceiver may include a processor configured to calculate an analyte level in a second medium using at least the one or more analyte measurements and the one or more interferent measurements.

Another aspect of the invention may provide an analyte monitoring system including an analyte sensor and a transceiver. The analyte sensor may include one or more analyte detectors configured to generate one or more analyte measurements indicative of an analyte level in a first medium. The analyte sensor may include a transceiver interface configured to convey the one or more analyte measurements. The transceiver may include a sensor interface configured to receive the one or more analyte measurements from the analyte sensor. The transceiver may include one or more interferent sensors configured to generate one or more interferent measurements indicative of an interferent level in the first medium. The transceiver may include a processor configured to calculate an analyte level in a second medium using at least the one or more analyte measurements and the one or more interferent measurements.

In some aspects, calculating the analyte level in the second medium may include calculating an analyte level in the first medium using at least the one or more analyte measurements. In some aspects, calculating the analyte level in the second medium may include calculating an interferent level in the first medium using at least the one or more interferent measurements. In some aspects, calculating the analyte level in the second medium may include calculating the analyte level in the second medium using at least the calculated analyte level in the first medium and the calculated interferent level in the first medium.

In some aspects, calculating the analyte level in the second medium using at least the calculated analyte level in the first medium and the calculated interferent level in the first medium may include adjusting one or more parameters of a conversion function based on at least the calculated interferent level in the first medium. In some aspects, calculating the analyte level in the second medium using at least the calculated analyte level in the first medium and the calculated interferent level in the first medium may include using at least the adjusted conversion function and the calculated analyte level in the first medium to calculate the analyte level in the second medium.

In some aspects, the analyte sensor may further include an analyte indicator and an interferent indicator. In some aspects, the analyte indicator may include analyte indicator molecules, and the interferent indicator may include interferent indicator molecules. In some aspects, the analyte sensor may further include an indicator structure, and the analyte indicator molecules may be distributed throughout the indicator structure. In some aspects, the interferent indicator molecules may be distributed throughout the indicator structure. In some aspects, the analyte sensor may further include an analyte excitation light source configured to irradiate the analyte indicator with analyte excitation light, and the analyte indicator may be configured to, in response to being irradiated with the analyte excitation light, emit analyte emission light indicative of the analyte level in the first medium. In some aspects, the one or more analyte detectors may include an analyte photodetector configured to output an analyte signal indicative of an amount of the analyte emission light received by the analyte photodetector.

In some aspects, the analyte excitation light source may be further configured to irradiate the interferent indicator with the analyte excitation light, and the interferent indicator may be configured to, in response to being irradiated with the analyte excitation light, emit interferent emission light indicative of the interferent level in the first medium. In some aspects, the one or more interferent detectors may include an interferent photodetector configured to output an interferent signal indicative of an amount of the interferent emission light received by the interferent photodetector. In some aspects, the analyte sensor may further include an interferent excitation light source configured to irradiate the interferent indicator with interferent excitation light, a wavelength range of the analyte excitation light may be different than a wavelength range of the interferent excitation light, and the interferent indicator may be configured to, in response to being irradiated with the interferent excitation light, emit interferent emission light indicative of the interferent level in the first medium. In some aspects, the one or more interferent detectors may include an interferent photodetector configured to output an interferent signal indicative of an amount of the interferent emission light received by the interferent photodetector.

In some aspects, the interferent may be a first interferent, the one or more interferent measurements may be one or more first interferent measurements, the one or more interferent detectors may be one or more first interferent detectors, the analyte sensor may further include one or more second interferent detectors configured to generate one or more second interferent measurements indicative of a second interferent level in the first medium, the transceiver interface may be further configured to convey the one or more second interferent measurements, the sensor interface may be further configured to receive the one or more second interferent measurements from the analyte sensor, and the processor may be configured to calculate the analyte level in the second medium using at least the one or more analyte measurements, the one or more first interferent measurements, and the one or more second interferent measurements. In some aspects, the first medium may be interstitial fluid, the second medium may be blood, the analyte may be glucose, the first interferent may be insulin, and the second interferent may be blood.

In some aspects, the first medium may be interstitial fluid, the second medium may be blood, the analyte may be glucose, and the interferent may be insulin or blood.

Still another aspect of the invention may provide a method including using one or more analyte detectors of an analyte sensor to generate one or more analyte measurements indicative of an analyte level in a first medium. The method may include using one or more interferent detectors of the analyte sensor to generate one or more interferent measurements indicative of an interferent level in the first medium. The method may include using a transceiver interface of the analyte sensor to convey the one or more analyte measurements and the one or more interferent measurements. The method may include using a sensor interface of a transceiver to receive the one or more analyte measurements and the one or more interferent measurements from the analyte sensor. The method may include using the transceiver to calculate an analyte level in a second medium using at least the one or more analyte measurements and the one or more interferent measurements.

Still another aspect of the invention may provide a method including using one or more analyte detectors of an analyte sensor to generate one or more analyte measurements indicative of an analyte level in a first medium. The method may include using a transceiver interface of the analyte sensor to convey the one or more analyte measurements. The method may include using a sensor interface of a transceiver to receive the one or more analyte measurements. The method may include using one or more interferent sensors of the transceiver to generate one or more interferent measurements indicative of an interferent level in the first medium. The method may include using the transceiver to calculate an analyte level in a second medium using at least the one or more analyte measurements and the one or more interferent measurements.

In some aspects, calculating the analyte level in the second medium may include calculating an analyte level in the first medium using at least the one or more analyte measurements, calculating an interferent level in the first medium using at least the one or more interferent measurements, and calculating the analyte level in the second medium using at least the calculated analyte level in the first medium and the calculated interferent level in the first medium. In some aspects, calculating the analyte level in the second medium using at least the calculated analyte level in the first medium and the calculated interferent level in the first medium may include: adjusting one or more parameters of a conversion function based on at least the calculated interferent level in the first medium, and using at least the adjusted conversion function and the calculated analyte level in the first medium to calculate the analyte level in the second medium.

In some aspects, the method may further include using an analyte excitation light source of the analyte sensor to irradiate an analyte indicator of the analyte sensor with analyte excitation light. The method may further include using the analyte indicator to emit analyte emission light indicative of the analyte level in the first medium in response to being irradiated with the analyte excitation light. In some aspects, the one or more analyte detectors may include an analyte photodetector, and using the one or more analyte detectors to generate the one or more analyte measurements indicative of the analyte level in the first medium may include using the analyte photodetector to output an analyte signal indicative of an amount of the analyte emission light received by the analyte photodetector. In some aspects, the method may further include using the analyte excitation light source to irradiate an interferent indicator of the analyte sensor with the analyte excitation light, and using the interferent indicator to emit interferent emission light indicative of the interferent level in the first medium in response to being irradiated with the analyte excitation light. In some aspects, the one or more interferent detectors may include an interferent photodetector, and using the one or more interferent detectors to generate the one or more interferent measurements indicative of the interferent level in the first medium may include using the interferent photodetector to output an interferent signal indicative of an amount of the interferent emission light received by the interferent photodetector.

In some aspects, the method may further include using an interferent excitation light source of the analyte sensor to irradiate an interferent indicator of the analyte sensor with interferent excitation light, and a wavelength range of the analyte excitation light may be different than a wavelength range of the interferent excitation light. The method may further include using the interferent indicator emit interferent emission light indicative of the interferent level in the first medium in response to being irradiated with the interferent excitation light. In some aspects, the one or more interferent detectors may include an interferent photodetector, and using the one or more interferent detectors to generate the one or more interferent measurements indicative of the interferent level in the first medium may include using the interferent photodetector to output an interferent signal indicative of an amount of the interferent emission light received by the interferent photodetector.

In some aspects, the interferent may be a first interferent, the one or more interferent measurements may be one or more first interferent measurements, the one or more interferent detectors may be one or more first interferent detectors, and the method may further include using one or more second interferent detectors of the analyte sensor to generate one or more second interferent measurements indicative of a second interferent level in the first medium. The method may further include using the transceiver interface of the analyte sensor to convey the one or more second interferent measurements. The method may further include using the sensor interface of the transceiver to receive the one or more second interferent measurements from the analyte sensor. The transceiver may use at least the one or more analyte measurements, the one or more first interferent measurements, and the one or more second interferent measurements to calculate the analyte level in the second medium. In some aspects, the first medium may be interstitial fluid, the second medium may be blood, the analyte may be glucose, the first interferent may be insulin, and the second interferent may be blood.

In some aspects, the first medium may be interstitial fluid, the second medium may be blood, the analyte may be glucose, and the interferent may be insulin or blood.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 7G, 7H, and 7I are schematic views illustrating analyte sensors including two or more indicator structures.

DETAILED DESCRIPTION OF PREFERRED EMBODIMENTS

Figure 1A:
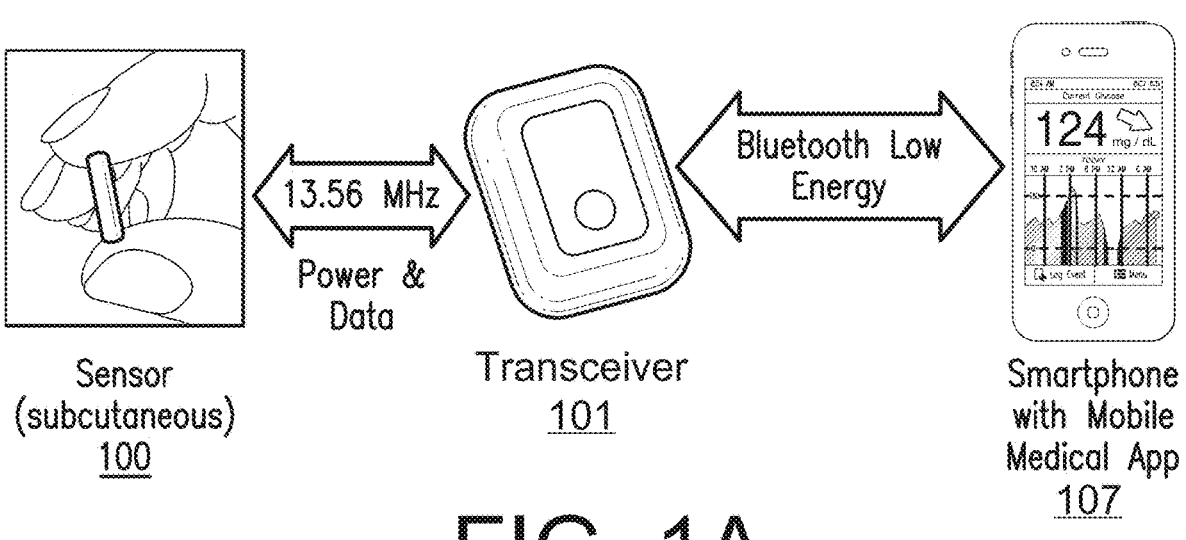
FIG. 1A is a schematic view illustrating an analyte monitoring system embodying aspects of the present invention.

FIG. 1A is a schematic view of an exemplary analyte monitoring system 50 embodying aspects of the present invention. The analyte monitoring system 50 may be a continuous analyte monitoring system (e.g., a continuous glucose monitoring system). In some aspects, the analyte monitoring system 50 may include one or more of an analyte sensor 100, a transceiver 101, and a display device 107. In some aspects, the sensor 100 may be a small, fully subcutaneously implantable sensor that takes one or more measurements indicative of analyte (e.g., glucose) levels in a first medium (e.g., interstitial fluid) of a living animal (e.g., a living human). However, this is not required, and, in some alternative aspects, the sensor 100 may be a partially implantable (e.g., transcutaneous) sensor or a fully external sensor.

In some embodiments, the transceiver 101 may be an externally worn device (e.g., attached via an armband, wristband, waistband, or adhesive patch). In some embodiments, the transceiver 101 may remotely power and/or communicate with the analyte sensor 100 (e.g., via near field communication (NFC)). However, this is not required, and, in some alternative embodiments, the transceiver 101 may power and/or communicate with the analyte sensor 100 via one or more wired connections. In some embodiments, the transceiver 101 may power and/or communicate with the analyte sensor 100 to initiate and receive the measurements from the analyte sensor 100. In some embodiments, the transceiver 101 may be a transceiver. In some non-limiting embodiments, the transceiver 101 may be a smartphone (e.g., an NFC-enabled smartphone). In some embodiments, the transceiver 101 may communicate information (e.g., one or more measurements) wirelessly (e.g., via a Bluetooth™ communication standard such as, for example and without limitation Bluetooth Low Energy) to a hand held application running on a display device 107 (e.g., smartphone).

Figure 1B:
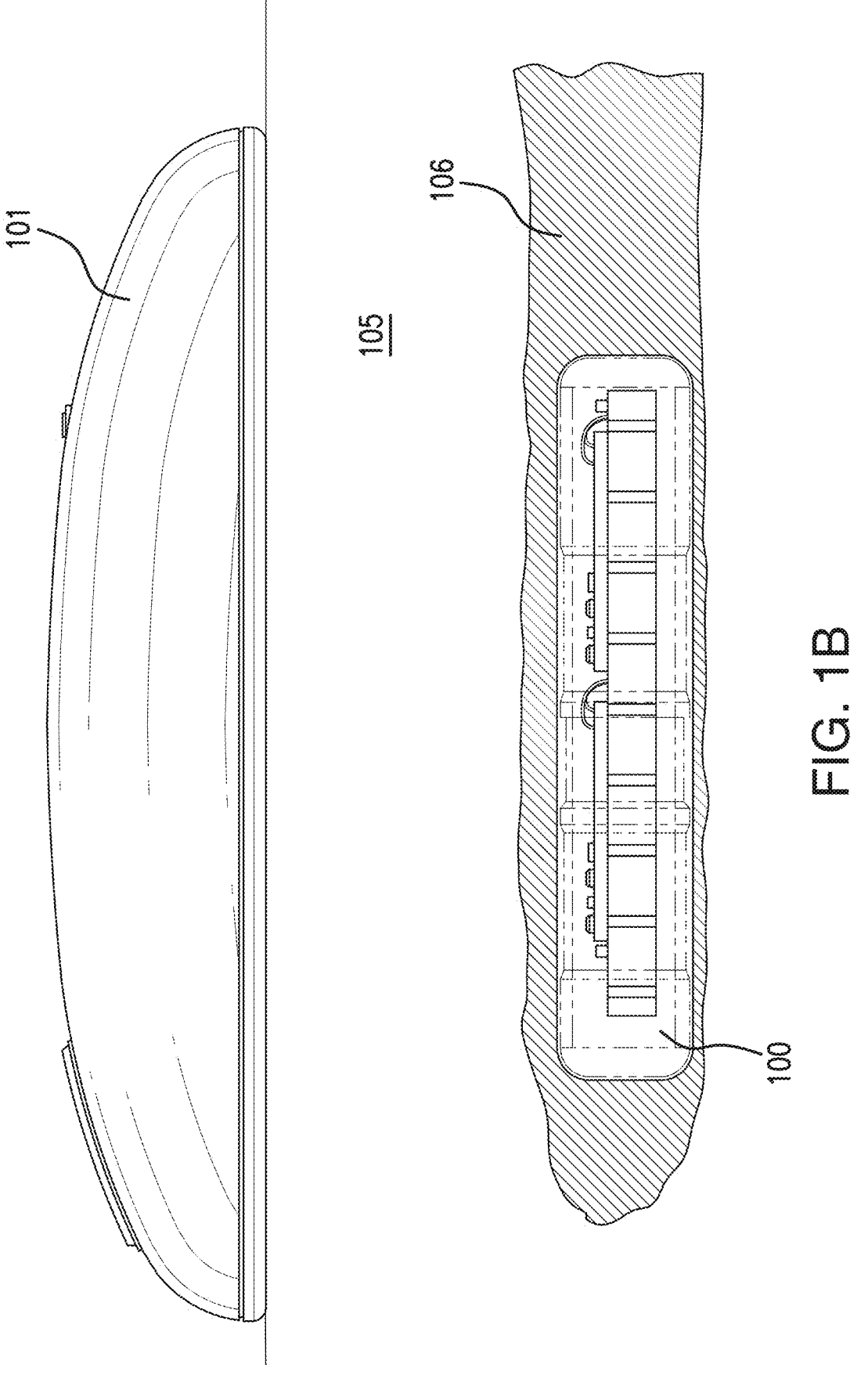
FIG. 1B is a schematic view illustrating an analyte sensor and a transceiver of an analyte monitoring system embodying aspects of the present invention.

In some non-limiting embodiments, as illustrated in FIG. 1B, when the system 50 is in use, the analyte sensor 100 may be implanted in the tissue 105 of the living animal, and the transceiver 101 may be external to the tissue 105. In some embodiments, the back of the transceiver 101 may be adjacent to the tissue 105 (e.g., adjacent to the skin of the living animal). As shown in FIG. 1B, in some non-limiting embodiments, after implantation, the analyte sensor 100 may rest in a pocket 106 in the tissue 105, and the pocket 106 may surround the analyte sensor 100. In some non-limiting embodiments, the pocket 106 may be created by a tissue dissector tool before implantation of the analyte sensor 100 or by the implantation process.

Figure 2A:
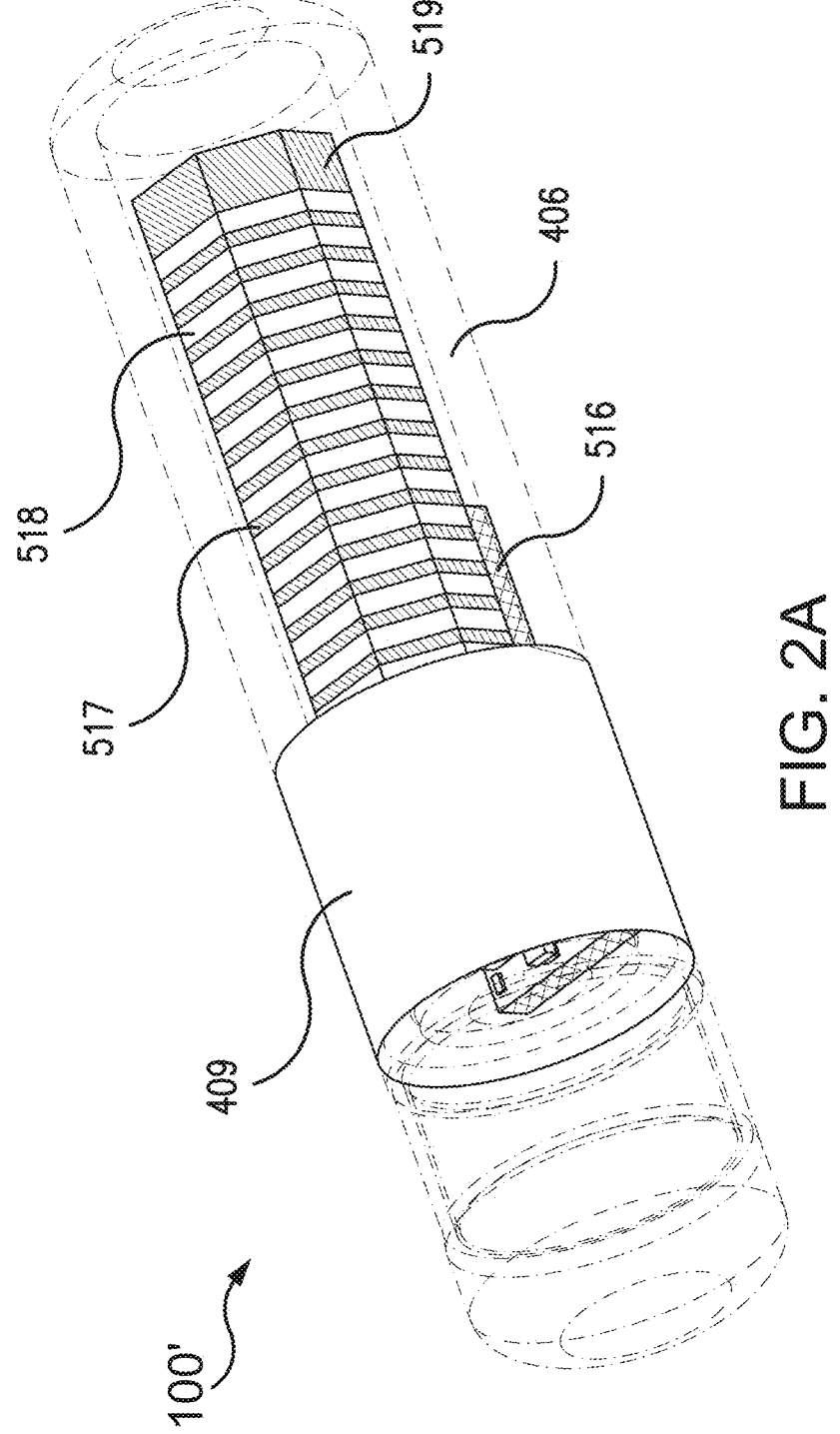
FIG. 2A is a perspective view illustrating a first non-limiting example of an implantable device embodying aspects of the present invention.
Figure 2B:
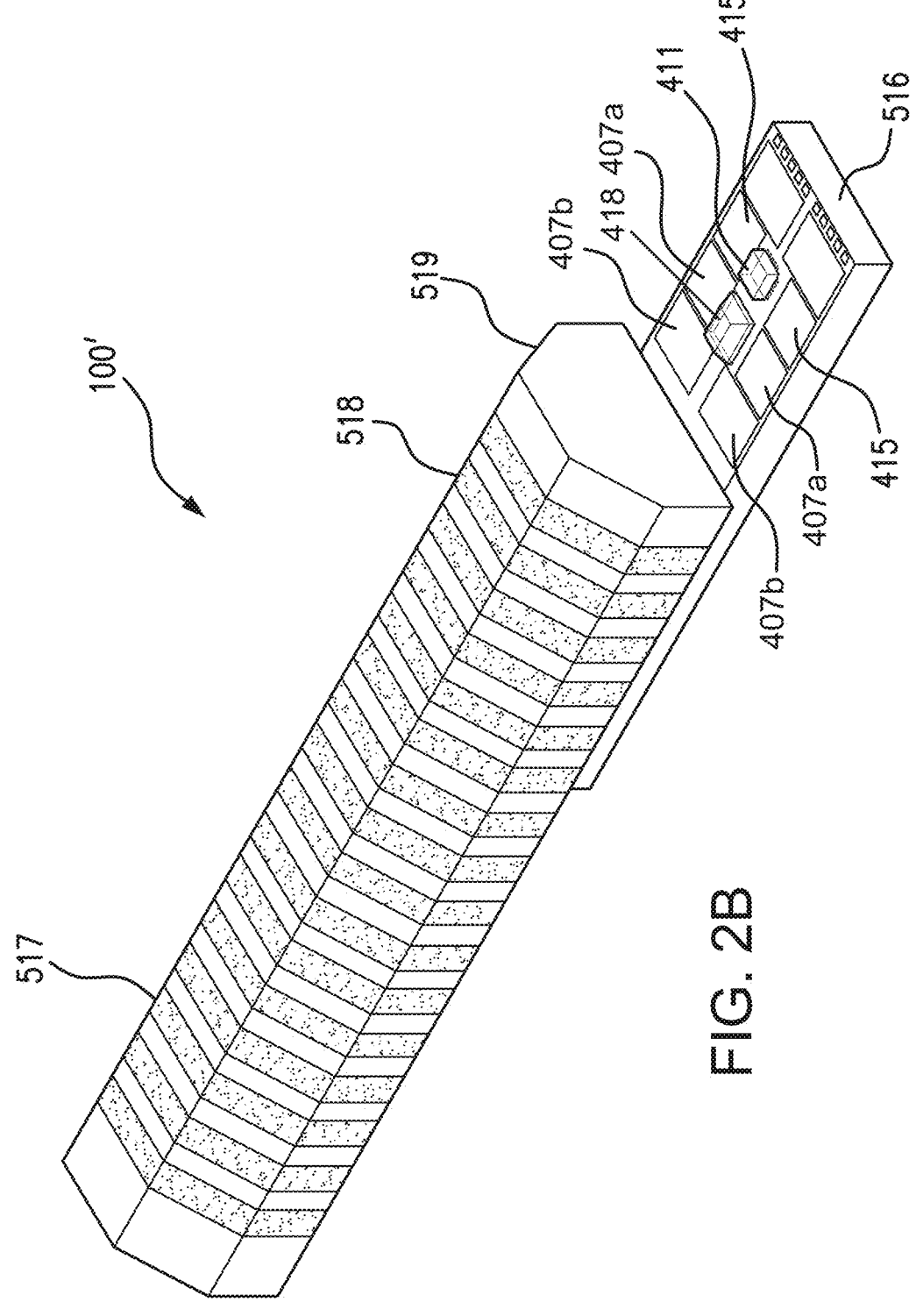
FIG. 2B is a perspective view illustrating elements of the first non-limiting example of the analyte sensor embodying aspects of the present invention.

FIG. 2A is a perspective view illustrating an analyte sensor 100' that is a first non-limiting example of the analyte sensor 100 of the system 50, and FIG. 2B is a perspective view illustrating elements of the analyte sensor 100'. In some non-limiting embodiments, as shown in FIG. 2A, the sensor 100 may include a housing 406 (i.e., body, shell, capsule, or encasement), which may be rigid and biocompatible. In one non-limiting embodiment, the housing 406 may be a silicon tube. However, this is not required, and, in other embodiments, different materials and/or shapes may be used for the housing 406. In some embodiments, the implantable device 100 may include a transmissive optical cavity. In some non-limiting embodiments, the transmissive optical cavity may be formed from a suitable, optically transmissive polymer material, such as, for example, acrylic polymers (e.g., polymethylmethacrylate (PMMA)). However, this is not required, and, in other embodiments, different materials may be used for the transmissive optical cavity.

In some embodiments, as shown in FIG. 2A, the analyte sensor 100 may include one or more indicator structures 409, such as, for example, a polymer graft or hydrogel coated, diffused, adhered, embedded, or grown on or in at least a portion of the exterior surface of the housing 406. In some non-limiting embodiments, the housing 406 may include one or more cutouts or recesses, and the one or more indicator structures 409 may be located (partially or entirely) in the cutouts or recesses. In some embodiments, the one or more indicator structures 409 may be porous and may allow the analyte (e.g., glucose) in the first medium (e.g., interstitial fluid) to diffuse into the one or more indicator structures 409.

In some embodiments, the analyte sensor 100 may include a transceiver interface for communicating with the transceiver 101. In some embodiments, the transceiver 101 may be an electronic device that communicates with the analyte sensor 100 to power the analyte sensor 100 and/or receive measurement data (e.g., photodetector and/or temperature sensor readings) from the analyte sensor 100. In some embodiments, the transceiver 101 may calculate one ore more analyte concentrations from the measurement data received from the analyte sensor 100. However, it is not required that the transceiver 101 perform the analyte concentration calculations itself, and, in some alternative embodiments, the transceiver 101 may additionally or alternatively convey/relay the measurement data received from the analyte sensor 100 to another device (e.g., the display device 107) for calculation of analyte concentrations. In other alternative embodiments, the analyte sensor 100 may perform the analyte concentration calculations and convey the calculated analyte concentrations to the transceiver 101.

In some embodiments, the transceiver interface of the analyte sensor 100 may include an antenna for wireless communication with the transceiver 101. In some of alternative embodiments (e.g., transcutaneous embodiments), the transceiver interface may include a wired connection between the analyte sensor 100 and the transceiver 101.

In some embodiments (e.g., embodiments in which the analyte sensor 100 is a fully implantable sensing system), the transceiver 101 may implement a passive telemetry for communicating with the analyte sensor 100 via an inductive magnetic link for power and/or data transfer. In some embodiments, as shown in FIGS. 2A and 2B, the transceiver interface of the analyte sensor 100 may include an inductor 517, which may be, for example, a ferrite based micro-antenna. In some embodiments, as shown in FIGS. 2A and 2B, the inductor 517 may include a conductor 518 in the form of a coil and a magnetic core 519. In some non-limiting embodiments, the core 519 may be, for example and without limitation, a ferrite core. In some embodiments, the inductor 517 may be connected to circuitry (e.g., an application specification integrated circuit (ASIC)) of the analyte sensor 100. In some embodiments, the analyte sensor 100 may not include a battery, and, as a result, the analyte sensor 100 may rely on the transceiver 101 to provide power for the analyte sensor 100 of the system 105 and a data link to convey data from the analyte sensor 100 to the transceiver 101.

In some non-limiting embodiments, the transceiver 101 may provide energy to run the analyte sensor 100 via a magnetic field. In some embodiments, the magnetic external device-implantable device link can be considered as "weakly coupled transformer" type. In some non-limiting embodiments, the transceiver 101 and analyte sensor 100 may communicate using near field communication (e.g., at a frequency of 13.56 MHz, which can achieve high penetration through the skin and is a medically approved frequency band) for power transfer. However, this is not required, and, in other embodiments, different frequencies may be used for powering and communicating with the analyte sensor 100.

Although in some embodiments, as illustrated in FIGS. 1A-2B, the analyte sensor 100 may be a fully implantable sensor, this is not required, and, in some alternative embodiments, the analyte sensor 100 may be a transcutaneous device having a wired connection to the transceiver 101. For example, in some alternative embodiments, the analyte sensor 100 may be located in or on a transcutaneous needle (e.g., at the tip thereof). In these embodiments, instead of wirelessly communicating using inductors, the analyte sensor 100 and transceiver 101 may communicate using one or more wires connected between the transceiver 101 and the transcutaneous needle that includes the analyte sensor 100. For another example, in some alternative embodiments, the analyte sensor 100 may be located in a catheter (e.g., for intravenous blood glucose monitoring) and may communicate (wirelessly or using wires) with the transceiver 101.

In some embodiments, as shown in FIGS. 2A and 2B, the analyte sensor 100 may include a substrate 516. In some non-limiting embodiments, the substrate 516 may be a circuit board (e.g., a printed circuit board (PCB) or flexible PCB) on which one or more of circuit components (e.g., analog and/or digital circuit components) may be mounted or otherwise attached. However, in some alternative embodiments, the substrate 516 may be a semiconductor substrate.

In some embodiments, as shown in FIG. 2B, the analyte sensor 100 may include one or more light sources (e.g., one or more analyte excitation light sources 411 and/or one or more interferent excitation light sources 418), and one or more of the light sources may be mounted on or fabricated within in the substrate 516. In some embodiments, the analyte sensor 100 may include one or more photodetectors (e.g., photodiodes, phototransistors, photoresistors, or other photosensitive elements), and one or more of the photodetectors may be mounted on or fabricated in the substrate 516. In some embodiments, the photodetectors may include one or more analyte photodetectors 415 and/or one or more interferent photodetectors 407. In some embodiments, the In some non-limiting embodiments, one or more light sources may be mounted on the substrate 516, one or more photodetectors may be fabricated within the substrate 516, and all or a portion of the circuit components may be fabricated within the substrate 516.

Although the analyte sensor 100' illustrated in FIGS. 2A and 2B has one substrate 516, this is not required, and, in some alternative embodiments, the analyte sensor 100' may include more than one substrate 516 (e.g., more than one semiconductor substrate). In some non-limiting alternative embodiments, a portion of the photodetectors (e.g., one or more photodetectors 415) may be on or in a first substrate, and a portion of the photodetectors (e.g., one or more photodetectors 407) may be on or in a second substrate that is separate and distinct from the first substrate. In some non-limiting alternative embodiments, one or more light sources (e.g., one or more analyte excitation light sources 411) may be on the first substrate, and one or more light sources (e.g., one or more interferent excitation light sources 418) may be on the second substrate that is separate and distinct from the first substrate.

Figure 3:
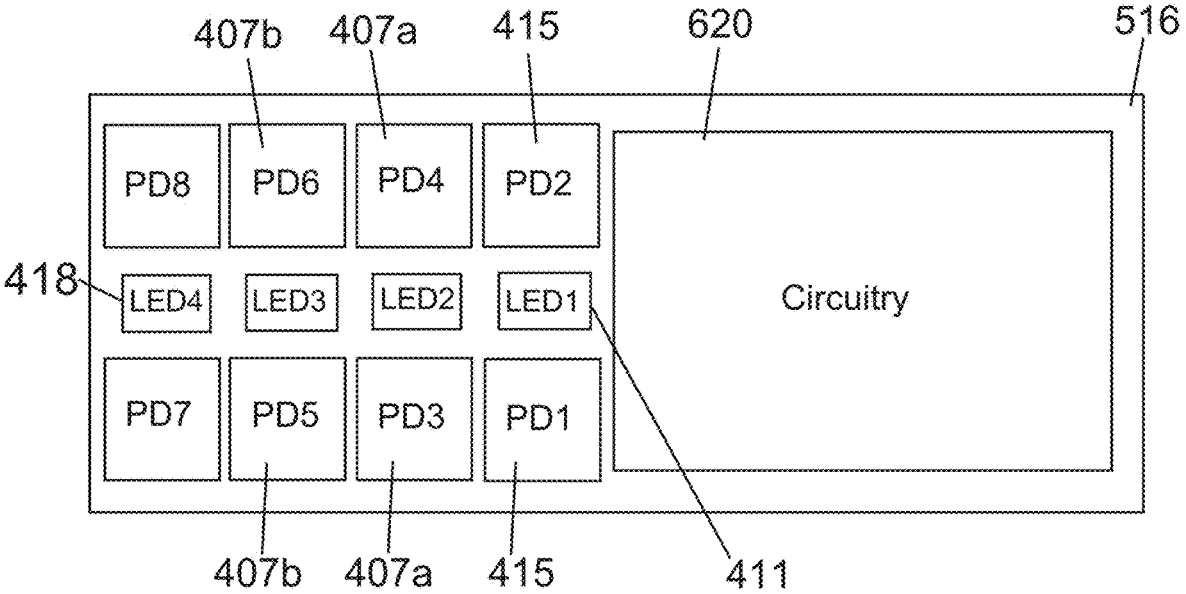
FIG. 3 is a schematic view illustrating the layout of a semiconductor substrate of an analyte sensor embodying aspects of the present invention.

FIG. 3 is a schematic view illustrating the layout of substrate 516 that is a semiconductor substrate embodying aspects of the present invention. As shown in FIG. 3, the semiconductor substrate 516 may have one or more of circuit components fabricated therein. For instance, the fabricated circuit components 620 may include analog and/ or digital circuitry. Also, in some embodiments in which the substrate 516 is a semiconductor substrate, in addition to the circuit components 620 fabricated in the semiconductor substrate, circuit components may be mounted or otherwise attached to the semiconductor substrate. In other words, in some semiconductor substrate embodiments, a portion or all of the circuit components, which may include discrete circuit elements, an integrated circuit (e.g., an application specific integrated circuit (ASIC)) and/or other electronic components (e.g., a non-volatile memory), may be fabricated in the semiconductor substrate with the remainder of the circuit components is secured to the semiconductor substrate, which may provide communication paths between the various secured components.

Figure 4:
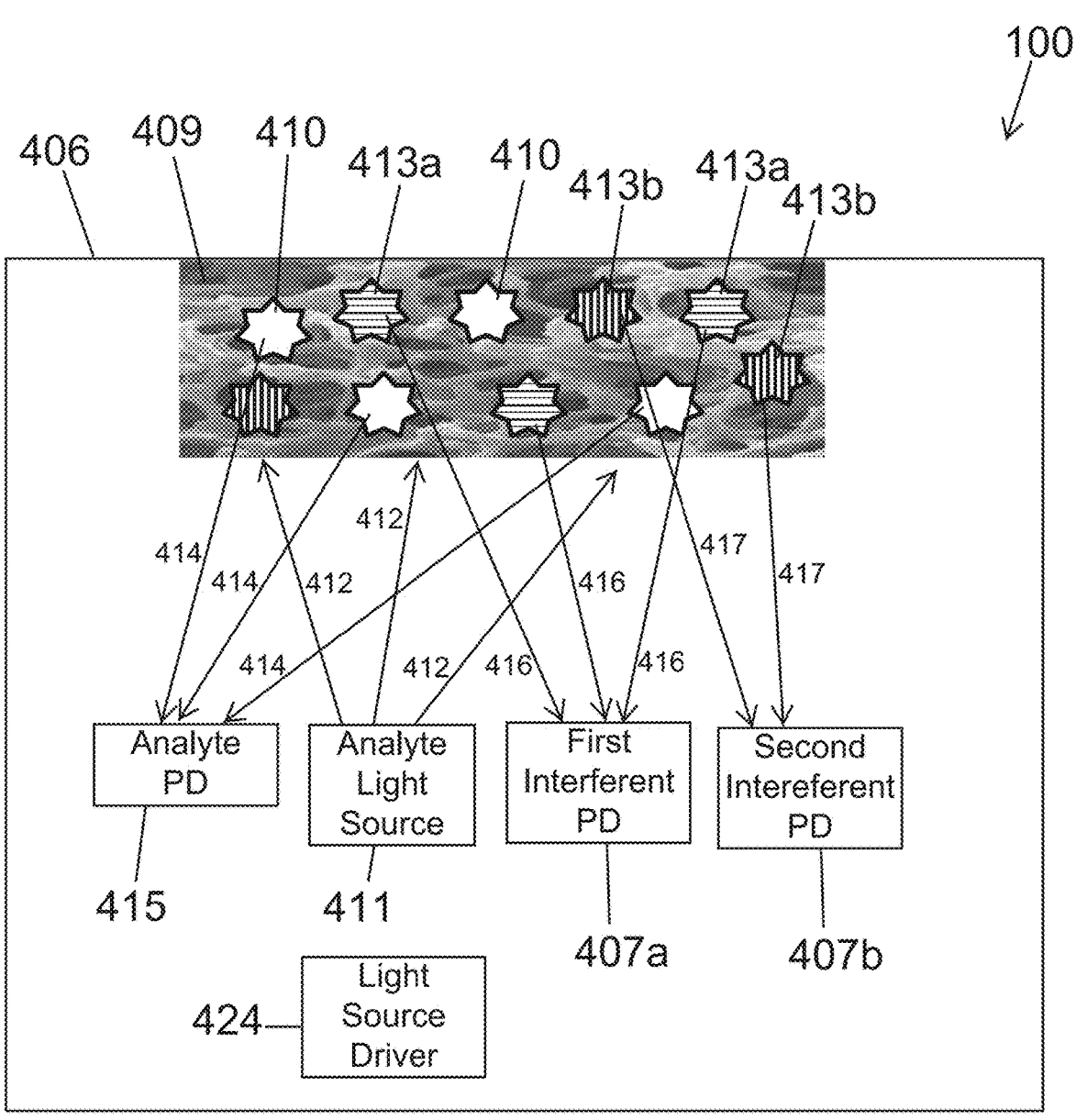
FIG. 4 is a schematic view of an analyte sensor including analyte photodetectors and interferent photodetectors and embodying aspects of the present invention.

In some embodiments, as shown in FIG. 4, the one or more indicator structures 409 (e.g., polymer grafts or hydrogels) of the analyte sensor 100 may include one or more analyte indicators 410. In some embodiments, the analyte indicator 410 may produce (e.g., exhibit) one or more detectable properties (e.g., optical properties) that vary in accordance with the amount or concentration of the analyte in proximity to the one or more indicator structures 409. In some non-limiting embodiments, in response to being irradiated with analyte excitation light 412, the analyte indicator 410 may emit an amount of analyte emission light 414 that varies in accordance with the amount or concentration of the analyte in proximity to the one or more indicator structures 409. In some embodiments, the analyte emission light 414 may be within an analyte emission wavelength range. In some embodiments, the analyte indicator 410 may include one or more analyte indicator molecules (e.g., fluorescent analyte indicator molecules), which may be distributed throughout the indicator structure 409. In some non-limiting embodiments, the one or more analyte indicator molecules may be configured to reversibly bind the analyte, and the one or more detectable properties produced may be indicative of whether the analyte is bound. In some non-limiting embodiments, the analyte emission light 414 may be fluorescent light. In some non-limiting embodiments, the analyte indicator 410 may be a phenylboronic-based analyte indicator. However, a phenylboronic-based analyte indicator is not required, and, in some alternative embodiments, the implantable device 100 may include a different analyte indicator, such as, for example and without limitation, a glucose oxidase-based indicator, a glucose dehydrogenase-based indicator, or a glucose binding protein-based indicator.

In some embodiments, as shown in FIG. 4, the analyte sensor 100 may include one or more analyte excitation light sources 411 that emit the analyte excitation light 412 over an excitation wavelength range of at least the analyte indicator 410. In some non-limiting embodiments, the wavelength range may include wavelengths that interact with at least the analyte indicator 410 in the indicator structure 409. In some non-limiting embodiments, the analyte excitation light 412 may be, for example and without limitation, ultraviolet (UV) light.

In some embodiments, the analyte sensor 100 may include one or more analyte detectors configured to detect a detectable property of the analyte indicator 410 and output an analyte signal indicative of the amount or concentration of the analyte in the medium within the living animal. In some embodiments, as shown in FIG. 4, the one or more analyte detectors of the analyte sensor 100 may include one or more analyte photodetectors 415. In some non-limiting embodiments, the one or more analyte photodetectors 415 may be configured to output an analyte signal indicative of an amount of the analyte emission light 414 received by the one or more analyte photodetectors 415. In some non-limiting embodiments, the one or more analyte photodetectors 415 may be configured to output an analyte signal indicative of an amount of the analyte emission light 414 received by the one or more analyte photodetectors 415 because one or more optical filters may prevent light outside the analyte emission wavelength range (i.e., light outside the wavelength range of the analyte emission light 414 emitted by the analyte indicator 410) from reaching the one or more analyte photodetectors 415. In some embodiments, as the amount of analyte emission light 414 emitted by the analyte indicator 410 varies in in accordance with the amount or concentration of the analyte in proximity to the indicator structure 409, the analyte signal output by the one or more analyte photodetectors 415 may be indicative of an amount or concentration of the analyte in the first medium in proximity to the indicator structure 409. In some embodiments, the circuit components (e.g., circuit components 620) of the analyte sensor 100 may include one or more circuit components (e.g., an analog-to-digital converter) configured to convert the analyte signal into one or more analyte measurements.

In some embodiments, one or more interferents (e.g., insulin or blood) in the first medium (e.g., interstitial fluid) may interfere with accurate measurement of the analyte (e.g., glucose) in the first medium. In some non-limiting embodiments, the analyte sensor 100 may measure the amount or concentration of one or more interferents in proximity to the one or more indicator structures 409. In some non-limiting embodiments, as shown in FIG. 4, the one or more indicator structures 409 of the analyte sensor 100 may include one or more interferent indicators 413 that may be used to measure the amount or concentration of one or more interferents. In some non-limiting embodiments, as shown in FIG. 4, the one or more indicator structures 409 of the analyte sensor 100 may include one or more of a first interferent indicator 413a and a second interferent indicator 413b that may be used to measure the amount or concentration of a first interferent and a second interferent, respectively.

In some embodiments, the first interferent indicator 413a may produce (e.g., exhibit) one or more detectable properties (e.g., optical properties) that vary in accordance with the amount or concentration of a first interferent in proximity to the one or more indicator structures 409. In some non-limiting embodiments, the first interferent indicator 413a may emit an amount of first interferent emission light 416 that varies in accordance with the amount or concentration of the first interferent in proximity to the one or more indicator structures 409. In some embodiments, the first interferent emission light 416 may be within a first interferent emission wavelength range. In some embodiments, the first interferent indicator 413a may include one or more first interferent indicator molecules (e.g., fluorescent interferent indicator molecules), which may be distributed throughout the indicator structure 409. In some non-limiting embodiments, the one or more first interferent indicator molecules may be configured to reversibly bind the first interferent, and the one or more detectable properties produced may be indicative of whether the first interferent is bound. In some non-limiting embodiments, the first interferent indicator 413a may be a phenylboronic-based interferent indicator. However, a phenylboronic-based interferent indicator is not required, and, in some alternative embodiments, the implantable device 100 may include a different first interferent indicator.

In some embodiments, the second interferent indicator 413b may produce (e.g., exhibit) one or more detectable properties (e.g., optical properties) that vary in accordance with the amount or concentration of a second interferent in proximity to the one or more indicator structures 409. In some non-limiting embodiments, the first and second interferents may be different interferents. In some non-limiting embodiments, the first interferent may be insulin, and the second interferent may be blood. In some non-limiting embodiments, the second interferent indicator 413b may emit an amount of second interferent emission light 417 that varies in accordance with the amount or concentration of the second interferent in proximity to the one or more indicator structures 409. In some embodiments, the second interferent emission light 417 may be within a second interferent emission wavelength range. In some embodiments, the second interferent indicator 413b may include one or more second interferent indicator molecules (e.g., fluorescent interferent indicator molecules), which may be distributed throughout the indicator structure 409. In some non-limiting embodiments, the one or more second interferent indicator molecules may be configured to reversibly bind the second interferent, and the one or more detectable properties produced may be indicative of whether the second interferent is bound. In some non-limiting embodiments, the second interferent indicator 413b may be a phenylboronic-based interferent indicator. However, a phenylboronic-based interferent indicator is not required, and, in some alternative embodiments, the implantable device 100 may include a different first interferent indicator.

In some embodiments, as shown in FIG. 4, the first interferent indicator 413a may emit the first interferent emission light 416 in response to being irradiated with the analyte excitation light 412 emitted by the one or more analyte excitation light sources 411. In some embodiments, the first excitation wavelength range of the analyte excitation light 412 may include wavelengths that interact with at least the first interferent indicator 413a in the indicator structure 409. In some embodiments, as shown in FIG. 4, the second interferent indicator 413b may emit the second interferent emission light 417 in response to being irradiated with the analyte excitation light 412 emitted by the one or more analyte excitation light sources 411. In some embodiments, the first excitation wavelength range of the analyte excitation light 412 may include wavelengths that interact with at least the second interferent indicator 413b in the indicator structure 409.

In some embodiments, the analyte sensor 100 may include one or more interferent detectors configured to detect a detectable property of the one or more interferent indicators 413 and output an interferent signal indicative of the amount or concentration of the interferent in the medium within the living animal. In some embodiments, as shown in FIG. 4, the one or more interferent detectors of the analyte sensor 100 may include one or more interferent photodetectors 407. In some embodiments, as shown in FIG. 4, the one or more interferent photodetectors 407 may include one or more first interferent photodetectors 407a. In some non-limiting embodiments, the one or more first interferent photodetectors 407a may be configured to output a first interferent signal indicative of an amount of the first interferent emission light 416 (e.g., fluorescent light) received by the one or more first interferent photodetectors 407a. In some non-limiting embodiments, the one or more first interferent photodetectors 407a may be configured to output a first interferent signal indicative of an amount of the first interferent emission light 416 received by the one or more first interferent photodetectors 407a because one or more optical filters may prevent light outside the wavelength range of the first interferent emission light 416 emitted by the first interferent indicator 413a from reaching the one or more first interferent photodetectors 407a. In some embodiments, the analyte emission wavelength range of the analyte emission light 414 may be different than the first interferent emission wavelength range of the first interferent emission light 416 (e.g., the analyte emission wavelength range and the first interferent emission wavelength range may be non-overlapping wavelength ranges). In some embodiments, as the amount of first interferent emission light 416 emitted by the first interferent indicator 413a varies in in accordance with the amount or concentration of the first interferent in proximity to the indicator structure 409, the first interferent signal output by the one or more first interferent photodetectors 407a may be indicative of an amount or concentration of a first interferent in a medium in proximity to the indicator structure 409. In some embodiments, the circuit components (e.g., circuit components 620) of the analyte sensor 100 may include one or more circuit components (e.g., an analog-to-digital converter) configured to convert the first interferent signal into one or more first interferent measurements.

In some embodiments, as shown in FIG. 4, the one or more interferent photodetectors 407 may additionally or alternatively include one or more second interferent photodetectors 407b. In some non-limiting embodiments, the one or more second interferent photodetectors 407b may be configured to output a second interferent signal indicative of an amount of the second interferent emission light 417 (e.g., fluorescent light) received by the one or more second interferent photodetectors 407b. In some non-limiting embodiments, the one or more second interferent photodetectors 407b may be configured to output a second interferent signal indicative of an amount of the second interferent emission light 417 received by the one or more second interferent photodetectors 407b because one or more optical filters may prevent light outside the wavelength range of the second interferent emission light 417 emitted by the second interferent indicator 413b from reaching the one or more second interferent photodetectors 407b. In some embodiments, the second interferent emission wavelength range of the second interferent emission light 417 may different than the analyte emission wavelength range of the analyte emission light 414 and different than the first interferent emission wavelength range of the first interferent emission light 416 (e.g., the wavelength ranges may be non-overlapping wavelength ranges). In some embodiments, as the amount of second interferent emission light 417 emitted by the second interferent indicator 413b varies in in accordance with the amount or concentration of the second interferent in proximity to the indicator structure 409, the second interferent signal output by the one or more second interferent photodetectors 407b may be indicative of an amount or concentration of a second interferent in the medium in proximity to the indicator structure 409. In some embodiments, the circuit components (e.g., circuit components 620) of the analyte sensor 100 may include one or more circuit components (e.g., an analog-to-digital converter) configured to convert the second interferent signal into one or more second interferent measurements.

In some embodiments, as shown in the FIG. 4, the analyte sensor 100 may include one or more light source drivers 424. In some embodiments, the one or more light source drivers 424 may be mounted on or fabricated in one or more substrates 516 of the analyte sensor 100 (e.g., one light source driver 424 per substrate 516). In some embodiments, the one or more light source drivers 424 may drive the one or more analyte excitation light sources 411 to emit the analyte excitation light 412. In some embodiments, the one or more light source drivers 424 may drive one or more of the analyte excitation light sources 411 under the control of one or more measurement controllers (e.g., a measurement controller may be mounted on or fabricated on each substrate 516 and may control any light source driver 424 mounted on or fabricated on the same substrate 516). In some non-limiting embodiments, all or a portion of one or more of the light source driver 424 and the measurement controller may be included in the circuit components 620 fabricated in a semiconductor substrate 516 of the analyte sensor 100 (see FIG. 3).

Figure 5A:
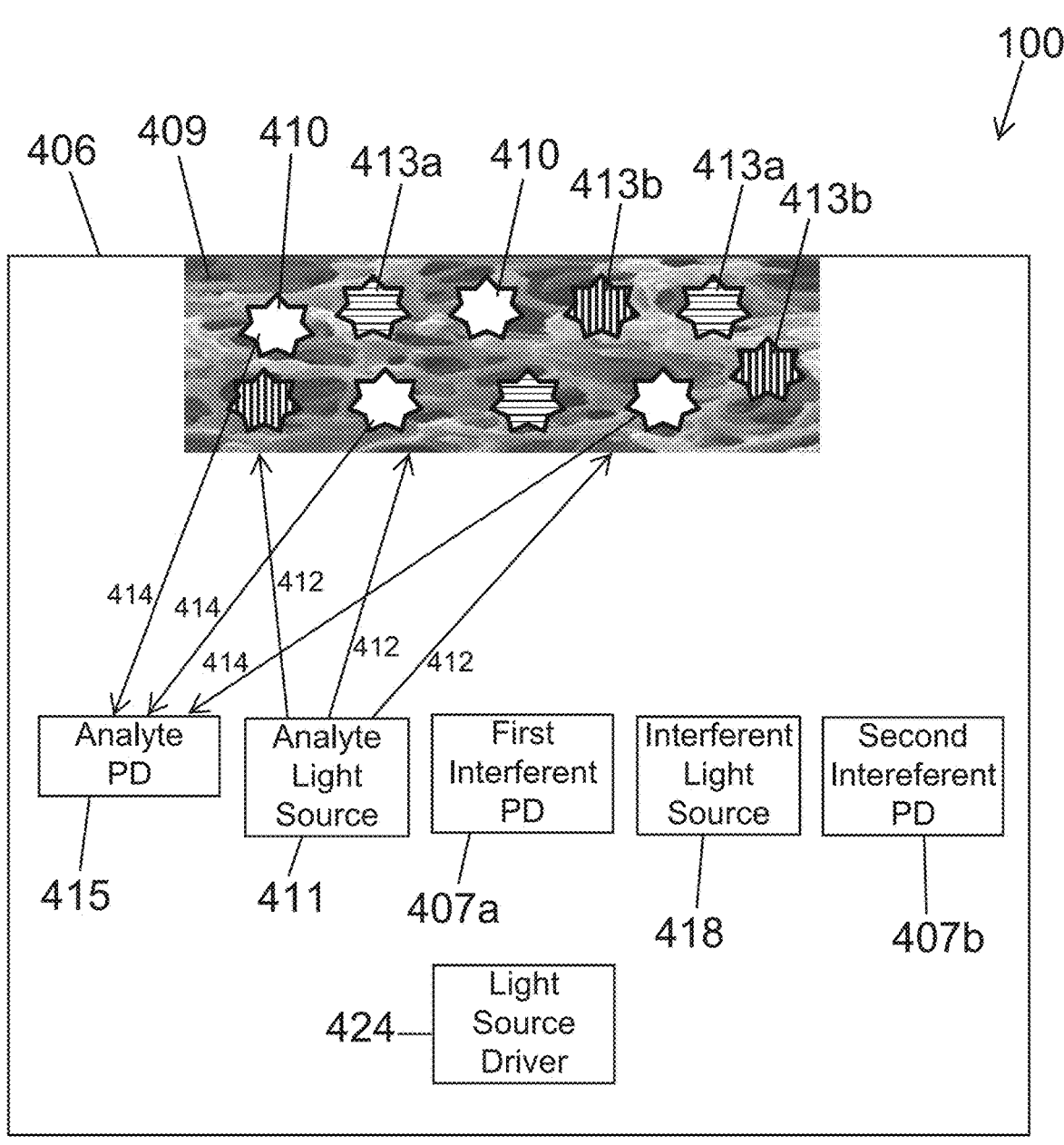
FIGS. 5A and 5B are schematic views of an analyte sensor including analyte photodetectors and interferent photodetectors and embodying aspects of the present invention.
Figure 5B:
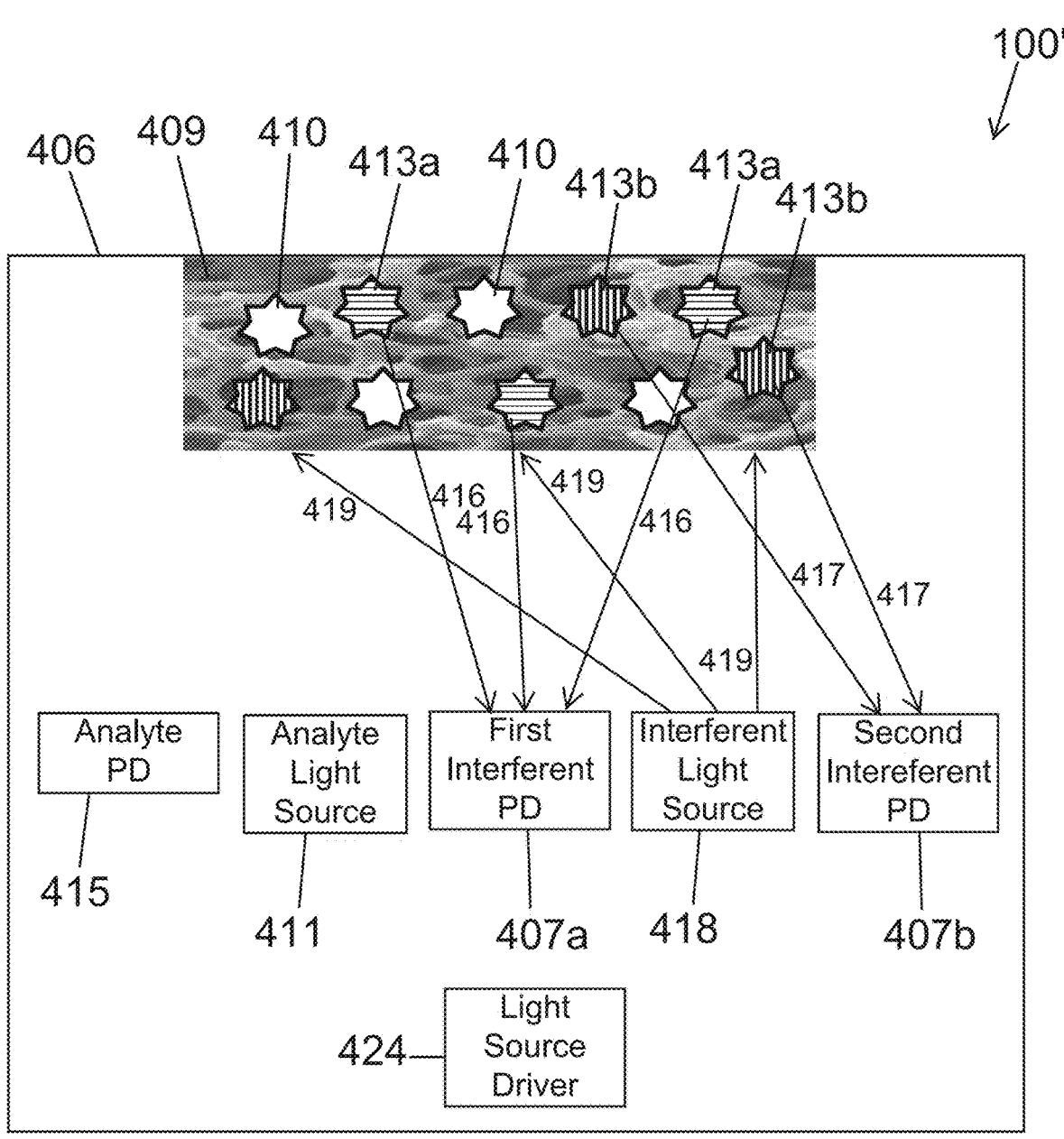

In some alternative embodiments, as shown in FIGS. 5A and 5B, the analyte sensor 100 may include one or more interferent excitation light sources 418. In some of these alternative embodiments, the wavelength range of the analyte excitation light source 411 may not include wavelengths that interact with one or more of the first and second interferent indicators 413a and 413b. In some of these alternative embodiments, as shown in FIG. 5A, the analyte indicator 410 may emit analyte emission light 412 in response to being irradiated by analyte excitation light 412, but the first and second interferent indicators 413a and 413b may not respond to the analyte emission light 412. In some embodiments, as shown in FIG. 5B, the one or more interferent excitation light sources 418 may emit interferent excitation light 419 over an excitation wavelength range of one or more of the first and second interferent indicators 413a and 413b. In some non-limiting embodiments, the wavelength range may include wavelengths that interact with one or more of the first and second interferent indicators 413a and 413b of the indicator structure 409. In some non-limiting embodiments, the interferent excitation light 419 may be, for example and without limitation, red or blue light. In some non-limiting embodiments, the wavelength range of the interferent excitation light 419 may be different than the wavelength range of the analyte excitation light 412. In some non-limiting embodiments, the wavelength range of the interferent excitation light 419 and the wavelength range of the analyte excitation light 412 may be non-overlapping wavelength ranges. In some of these alternative embodiments, as shown in FIG. 5B, the first and second interferent indicators 413a and 413b may emit first and second interferent emission light 416 and 417, respectively, in response to being irradiated by the interferent excitation light 419, but the analyte indicator 410 may not respond to the interferent excitation light 419.

In some embodiments, as shown in the FIGS. 5A and 5B, the one or more light source drivers 424 of the analyte sensor 100 may drive the one or more analyte excitation light sources 411 and/or the one or more interferent excitation light sources 418 to emit the analyte excitation light 412 and interferent excitation light 419, respectively. In some embodiments, the one or more light source drivers 424 may drive the one or more analyte excitation light sources 411 and/or the one or more interferent excitation light sources 418 under the control of one or more measurement controllers. In some embodiments, as shown in FIGS. 5A and 5B, the analyte sensor 100 (e.g., the measurement controller(s) and/or light source driver(s) 1424 of the implantable device 100) may be configured such that the one or more analyte excitation light sources 411 and the one or more interferent excitation light sources 418 emit the analyte excitation light 412 and interferent excitation light 419 at different times. For example, the one or more analyte excitation light sources 411 may emit the analyte excitation light 412 during first time periods, and the one or more interferent excitation light sources 418 may emit the interferent excitation light 419 during second time periods that are different than the first time periods. In one non-limiting embodiment, the analyte sensor 100 may cycle through the first and second time periods multiple times (e.g., 30 times) during a measurement period (e.g., 1 second). In some non-limiting embodiments, the cycle may additionally include third time periods during which both the analyte and interferent excitation light sources 411 and 418 are off. However, the analyte and interferent excitation light sources 411 and 418 are not required to emit the excitation light 412 and 419 at different times, and, in some alternative embodiments, the analyte sensor 100 (e.g., the measurement controller(s) and/or light source driver(s) 1424 of the implantable device 100) may be configured such that the one or more analyte excitation light sources 411 and the one or more interferent excitation light sources 418 emit the analyte excitation light 412 and interferent excitation light 419 simultaneously.

Figure 6A:
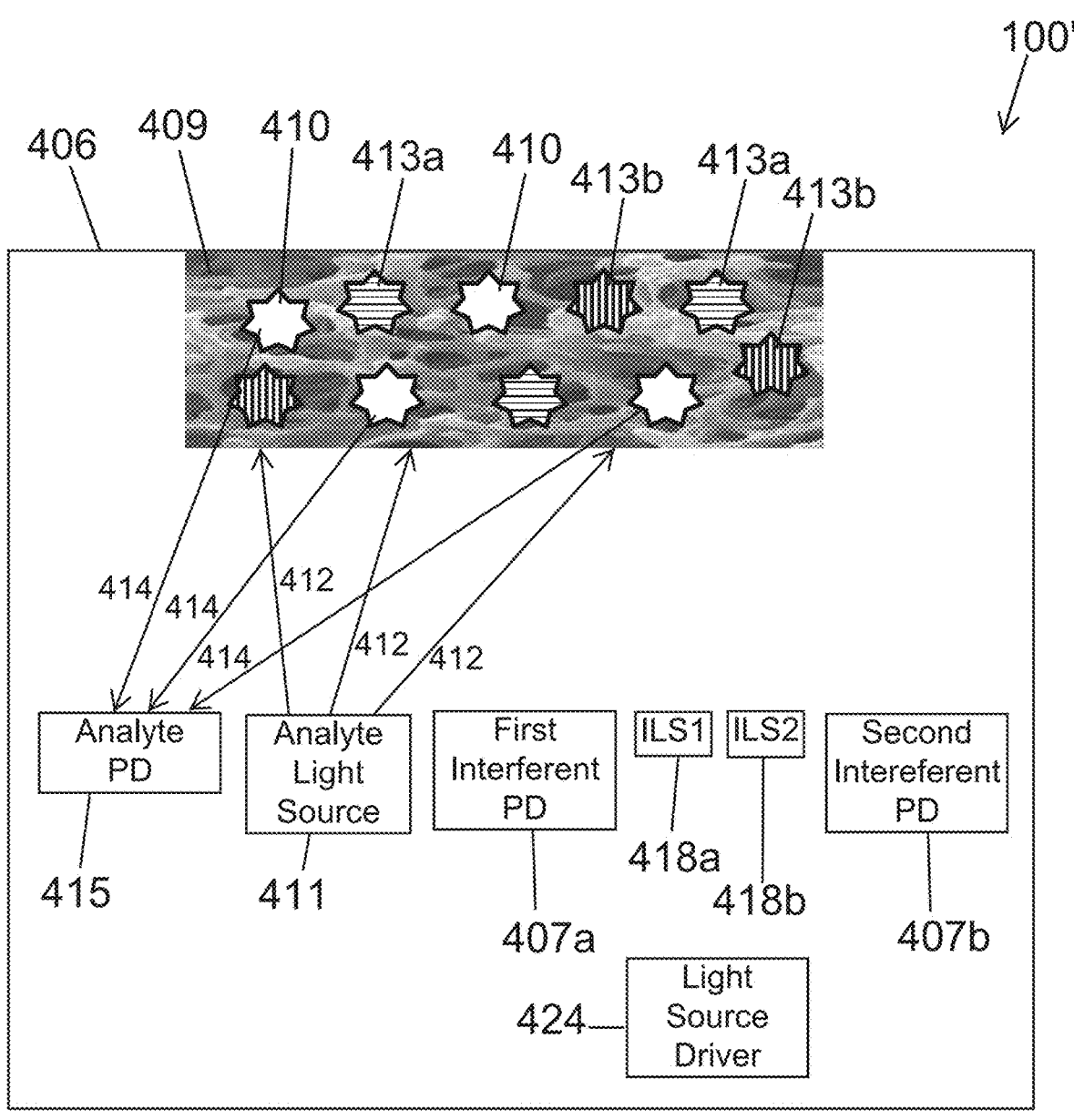
FIGS. 6A-6C are schematic views of an analyte sensor including analyte photodetectors and interferent photodetectors and embodying aspects of the present invention.
Figure 6B:
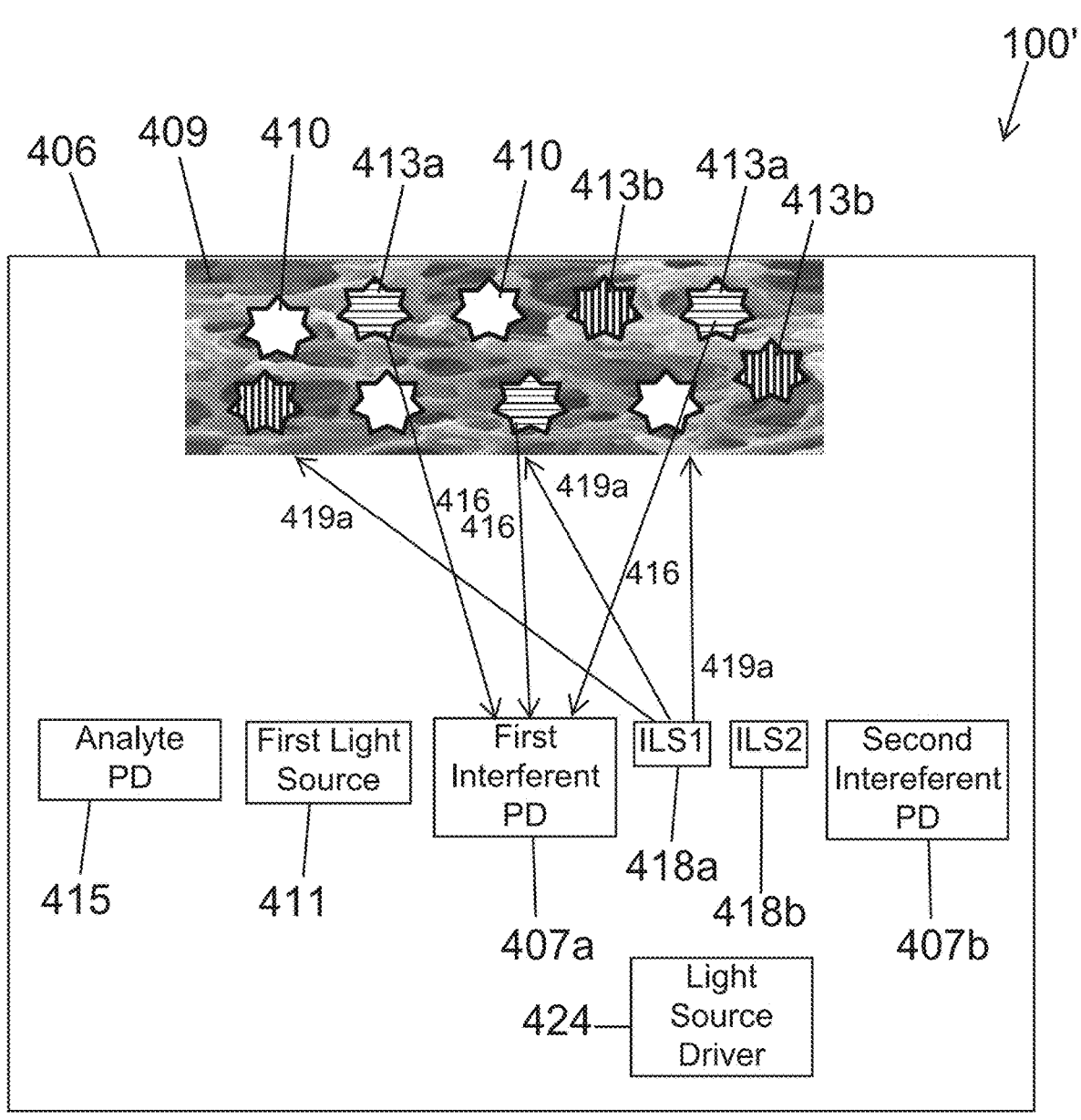
Figure 6C:
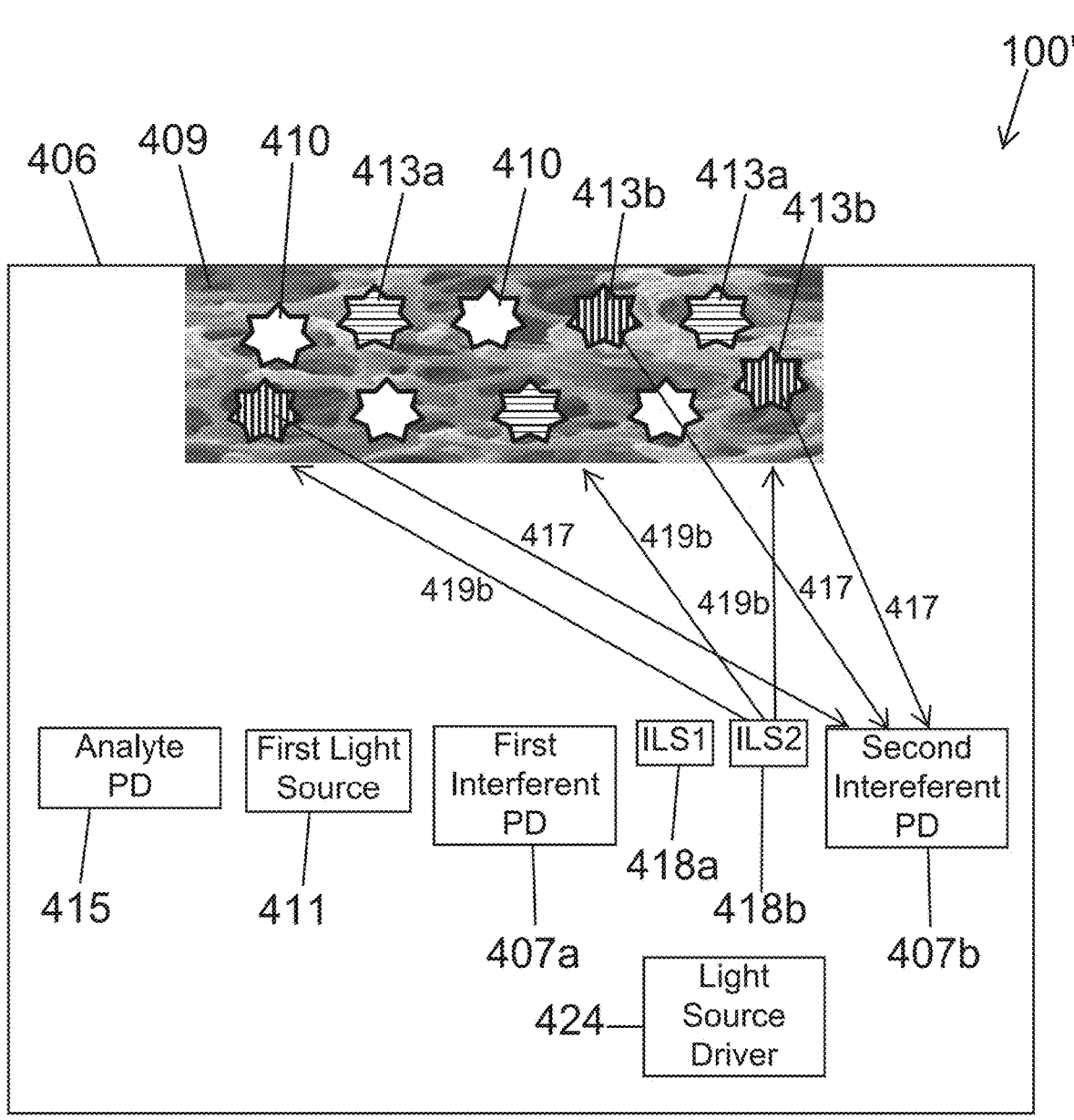

In some alternative embodiments, as shown in FIGS. 6A-6C, the analyte sensor 100 may include one or more first interferent excitation light sources 418a and one or more second interferent excitation light sources 418b. In some of these alternative embodiments, the wavelength range of the analyte excitation light source 411 may not include wavelengths that interact with the first and second interferent indicators 413a and 413b. In some of these alternative embodiments, as shown in FIG. 6A, the analyte indicator 410 may emit analyte emission light 412 in response to being irradiated by analyte excitation light 412, but the first and second interferent indicators 413a and 413b may not respond to the analyte emission light 412. In some of these alternative embodiments, as shown in FIG. 6B, the one or more first interferent excitation light sources 418a may emit first interferent excitation light 419a over an excitation wavelength range of the first interferent indicator 413a. In some non-limiting embodiments, the wavelength range may include wavelengths that interact with the first interferent indicator 413a of the indicator structure 409. In some of these alternative embodiments, as shown in FIG. 6B, the first interferent indicator 413a may emit first interferent emission light 416 in response to being irradiated by the first interferent excitation light 419a, but the analyte indicator 410 and the second interferent indicator 413b may not respond to the first interferent excitation light 419a. In some of these alternative embodiments, as shown in FIG. 6C, the one or more second interferent excitation light sources 418b may emit second interferent excitation light 419b over an excitation wavelength range of the second interferent indicator 413b. In some non-limiting embodiments, the wavelength range may include wavelengths that interact with the second interferent indicator 413b of the indicator structure 409. In some of these alternative embodiments, as shown in FIG. 6C, the second interferent indicator 413b may emit second interferent emission light 417 in response to being irradiated by the second interferent excitation light 419b, but the analyte indicator 410 and the first interferent indicator 413a may not respond to the second interferent excitation light 419b. In some non-limiting embodiments, the wavelength range of the analyte excitation light 412, the wavelength range of the first interferent excitation light 419a, and the wavelength range of the second interferent excitation light 419b may all be different. In some non-limiting embodiments, the wavelength range of the analyte excitation light 412, the wavelength range of the first interferent excitation light 419a, and the wavelength range of the second interferent excitation light 419b may be non-overlapping wavelength ranges.

In some embodiments, as shown in the FIGS. 6A-6C, the one or more light source drivers 424 of the analyte sensor 100 may drive the one or more analyte excitation light sources 411, the one or more first interferent excitation light sources 418a, and/or the one or more second interferent excitation light sources 418b to emit the analyte excitation light 412, the first interferent excitation light 419a, and the second interferent excitation light 419b, respectively. In some embodiments, the one or more light source drivers 424 may drive the one or more analyte excitation light sources 411, the one or more first interferent excitation light sources 418a, and the one or more second interferent excitation light sources 418b under the control of one or more measurement controllers. In some embodiments, as shown in FIGS. 6A-6C, the analyte sensor 100 (e.g., the measurement controller(s) and/or light source driver(s) 1424 of the implantable device 100) may be configured such that the one or more analyte excitation light sources 411, the one or more first interferent excitation light sources 418a, and the one or more second interferent excitation light sources 418b emit the analyte excitation light 412, the first interferent excitation light 419a, and the second interferent excitation light 419b at different times. For example, the one or more analyte excitation light sources 411 may emit the analyte excitation light 412 during first time periods, the one or more first interferent excitation light sources 418a may emit the first interferent excitation light 419a during second time periods that are different than the first time periods, and the one or more second interferent excitation light sources 418b may emit the second interferent excitation light 419 during third time periods that are different than the first and second time periods. In one non-limiting embodiment, the analyte sensor 100 may cycle through the first, second, and third time periods multiple times (e.g., 30 times) during a measurement period (e.g., 1 second). In some non-limiting embodiments, the cycle may additionally include fourth time periods during which all of the analyte and interferent excitation light sources 411, 418a, and 418b are off. However, the analyte and interferent excitation light sources 411, 418a, and 418b are not required to emit the excitation light 412 and 419 at different times, and, in some alternative embodiments, the analyte sensor 100 (e.g., the measurement controller(s) and/or light source driver(s) 1424 of the implantable device 100) may be configured such that the one or more analyte excitation light sources 411, the one or more first interferent excitation light sources 418a, and the one or more second interferent excitation light sources 418b emit the analyte excitation light 412, the first interferent excitation light 419a, and the second interferent excitation light 419b simultaneously. In some other alternative embodiments, the analyte sensor 100 may be configured such that two of the excitation light sources 411, 418a, and 418b (e.g., the first and second interferent excitation light sources 418a and 418b) emit excitation light (e.g., the first and second interferent excitation light 419a and 419b) simultaneously and the other one of the excitation light sources 411, 418a, and 418b (e.g., the analyte excitation light source 411) emits analyte excitation light 412 at a different time.

Figure 7A:
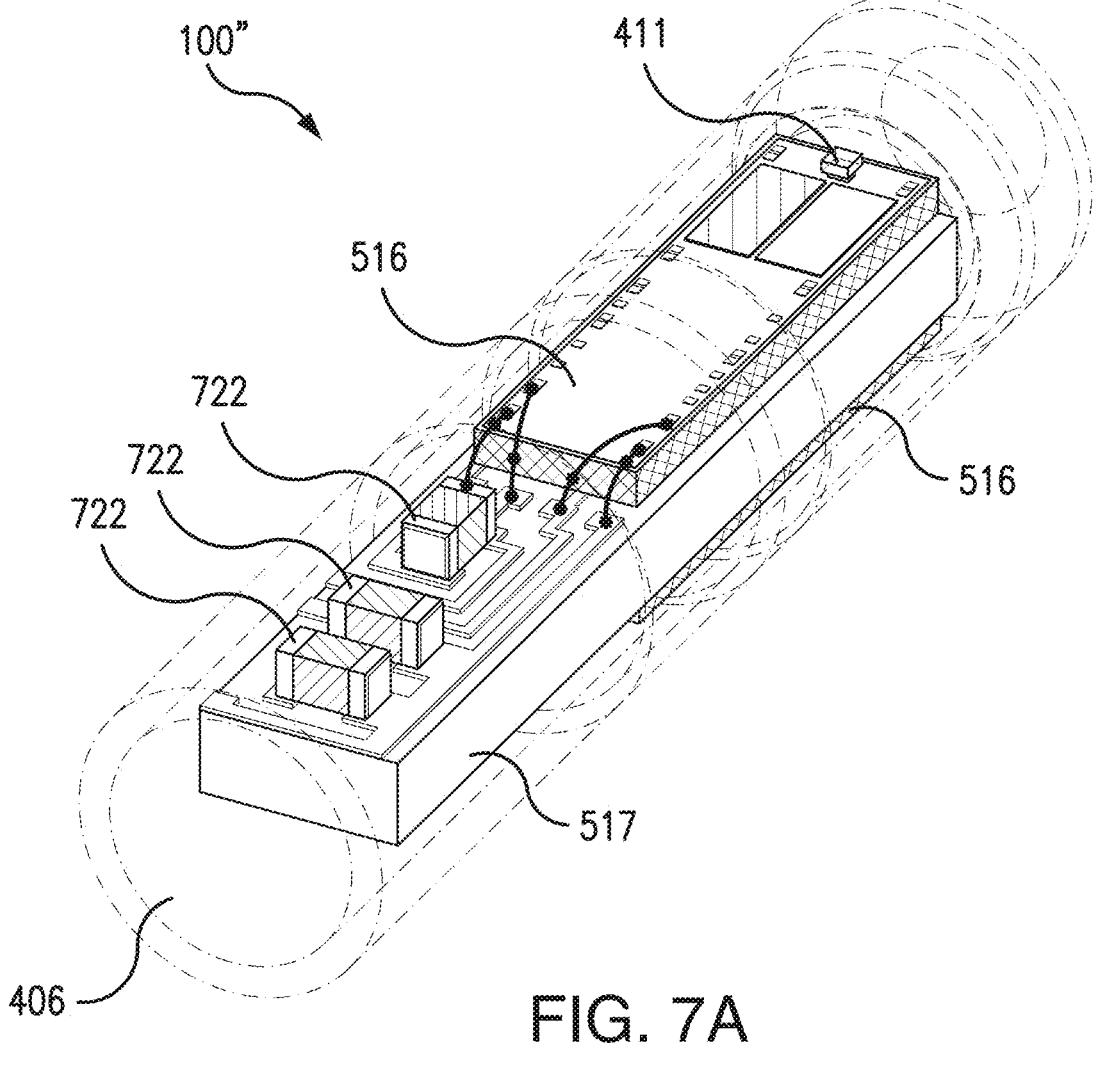
FIGS. 7A, 7B, and 7C are perspective, side, and cross-sectional views, respectively, of a second non-limiting example of an analyte sensor embodying aspects of the present invention.
Figure 7B:
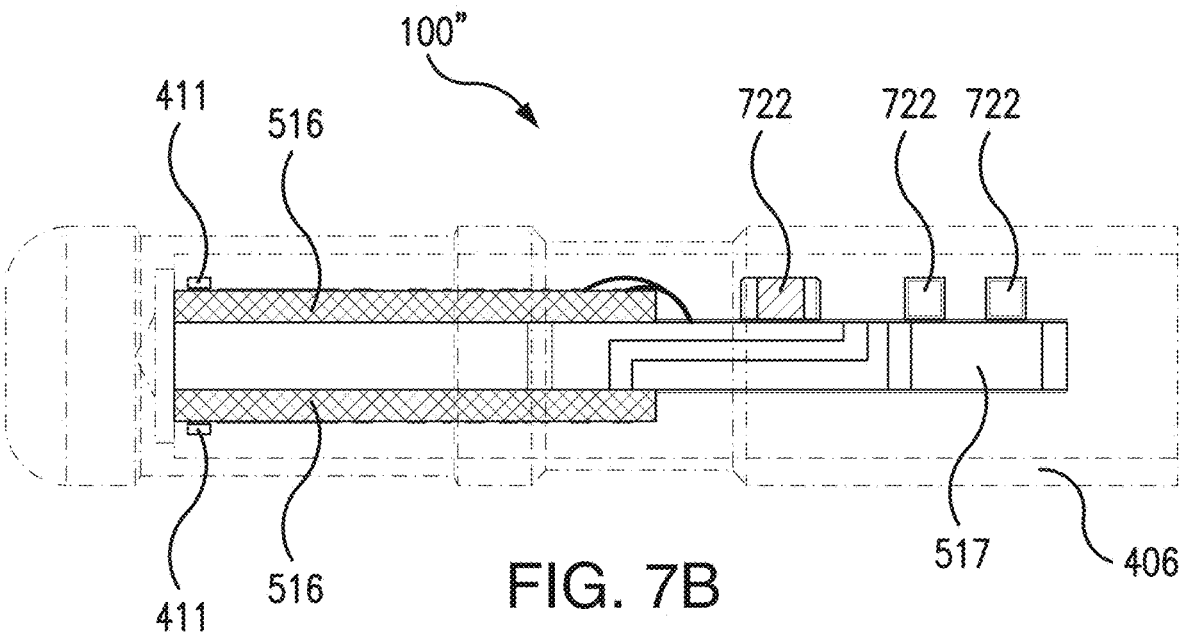
Figure 7C:
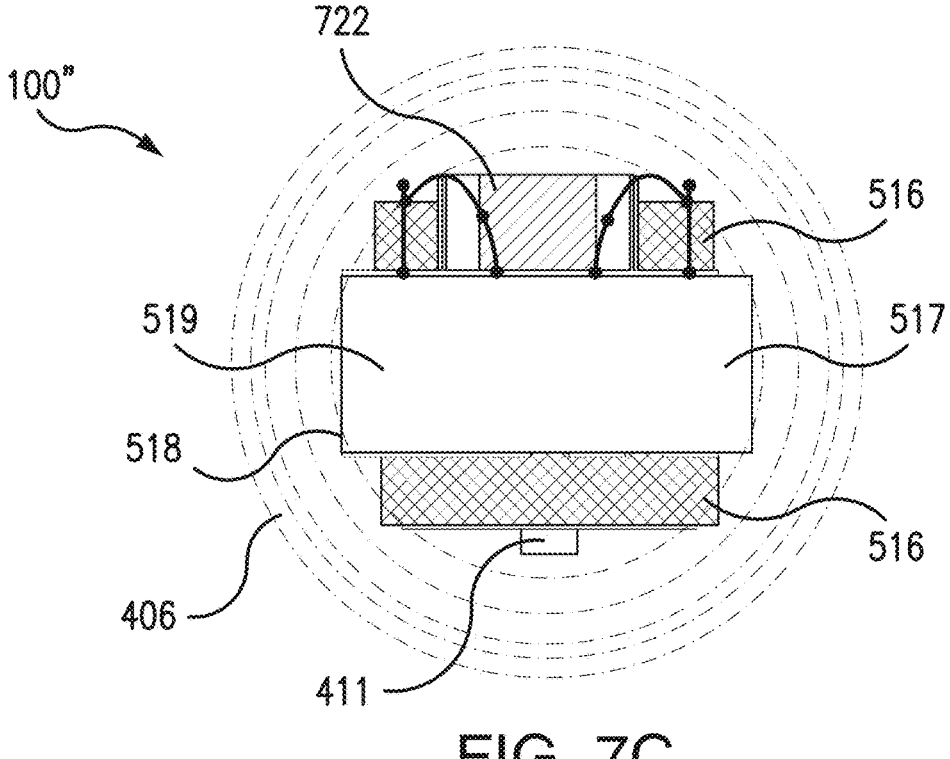
Figure 7D:
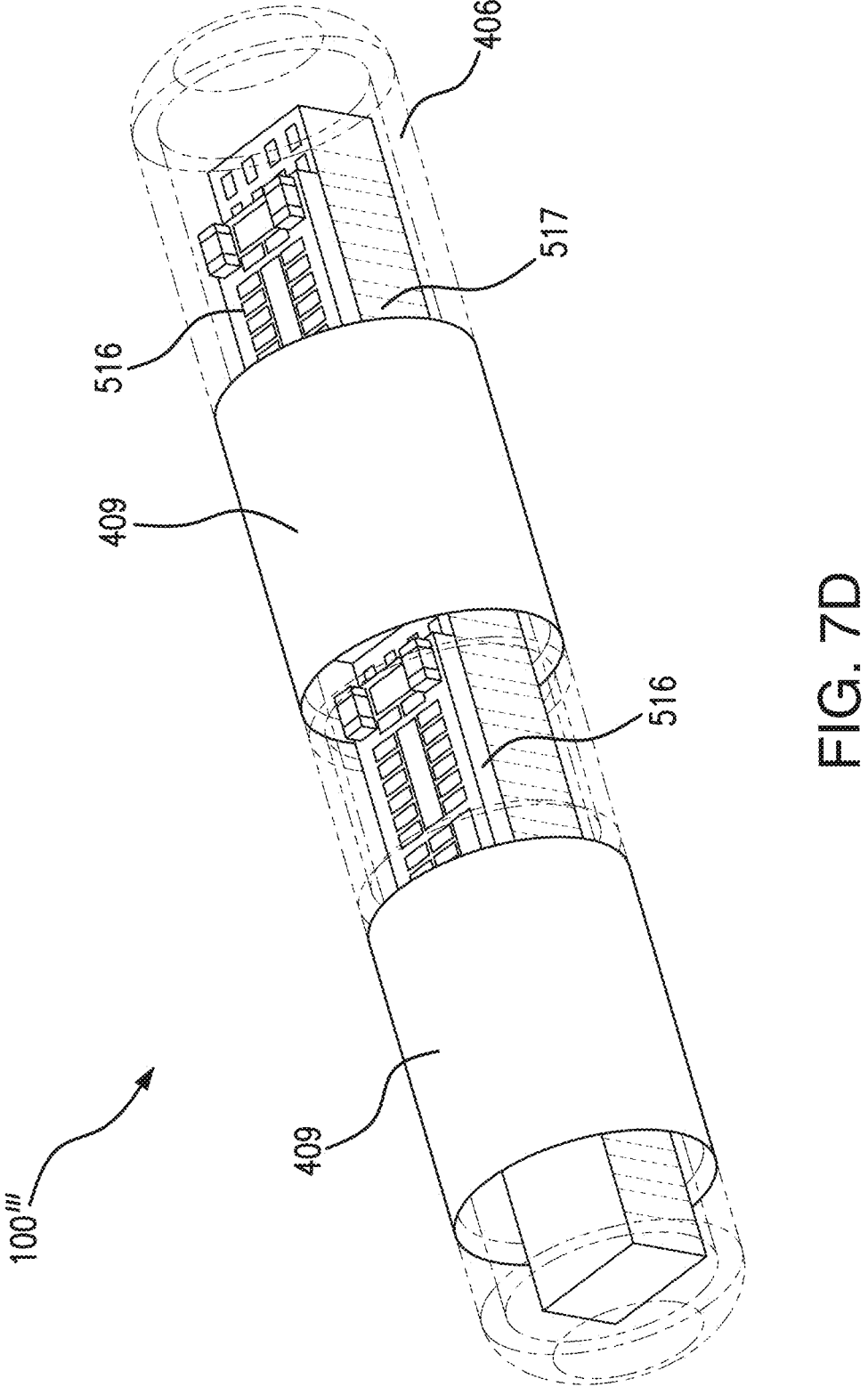
FIGS. 7D, 7E, and 7F are perspective, perspective, and side views, respectively, of a third non-limiting analyte sensor embodying aspects of the present invention.
Figure 7E:
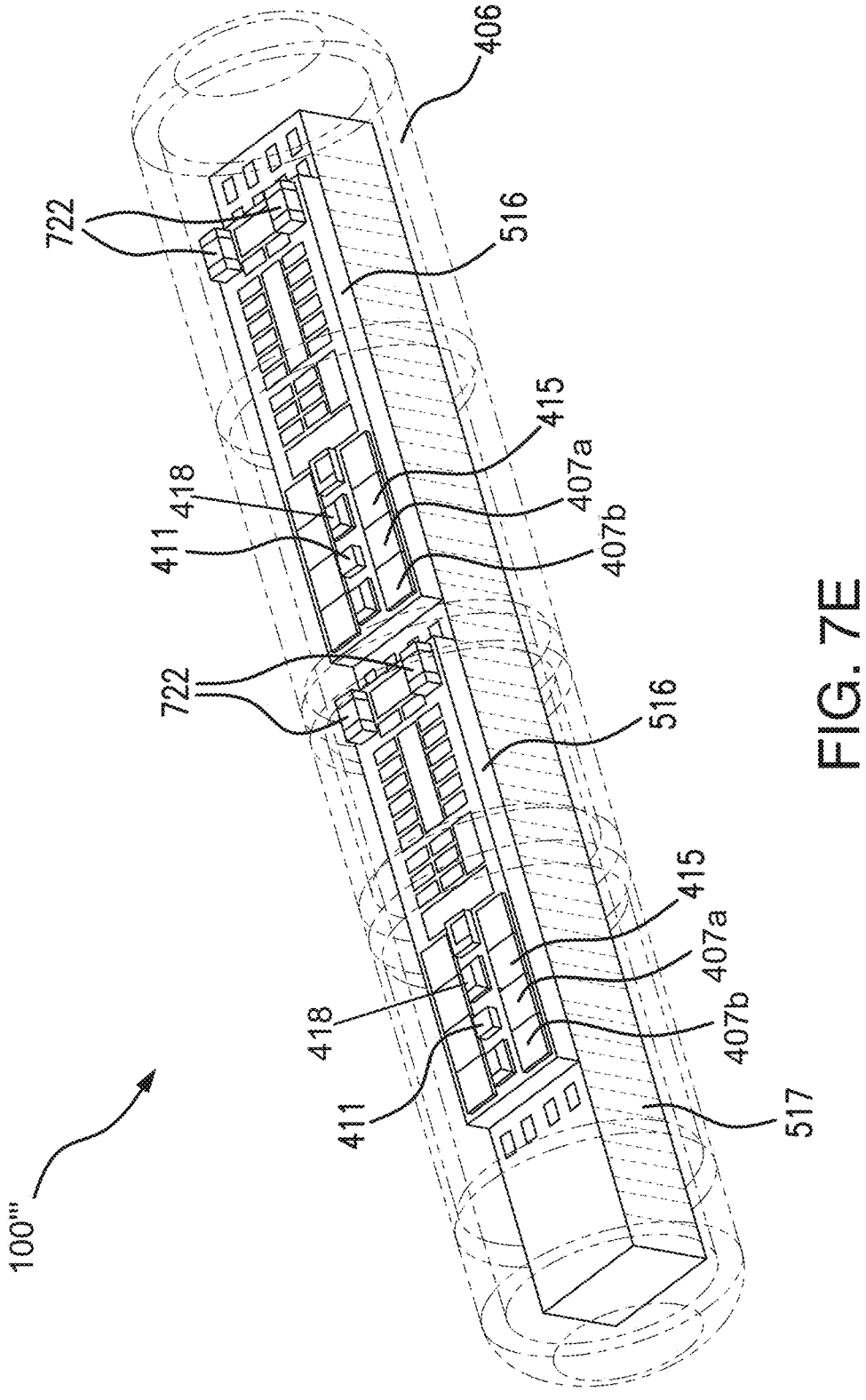
Figure 7F:
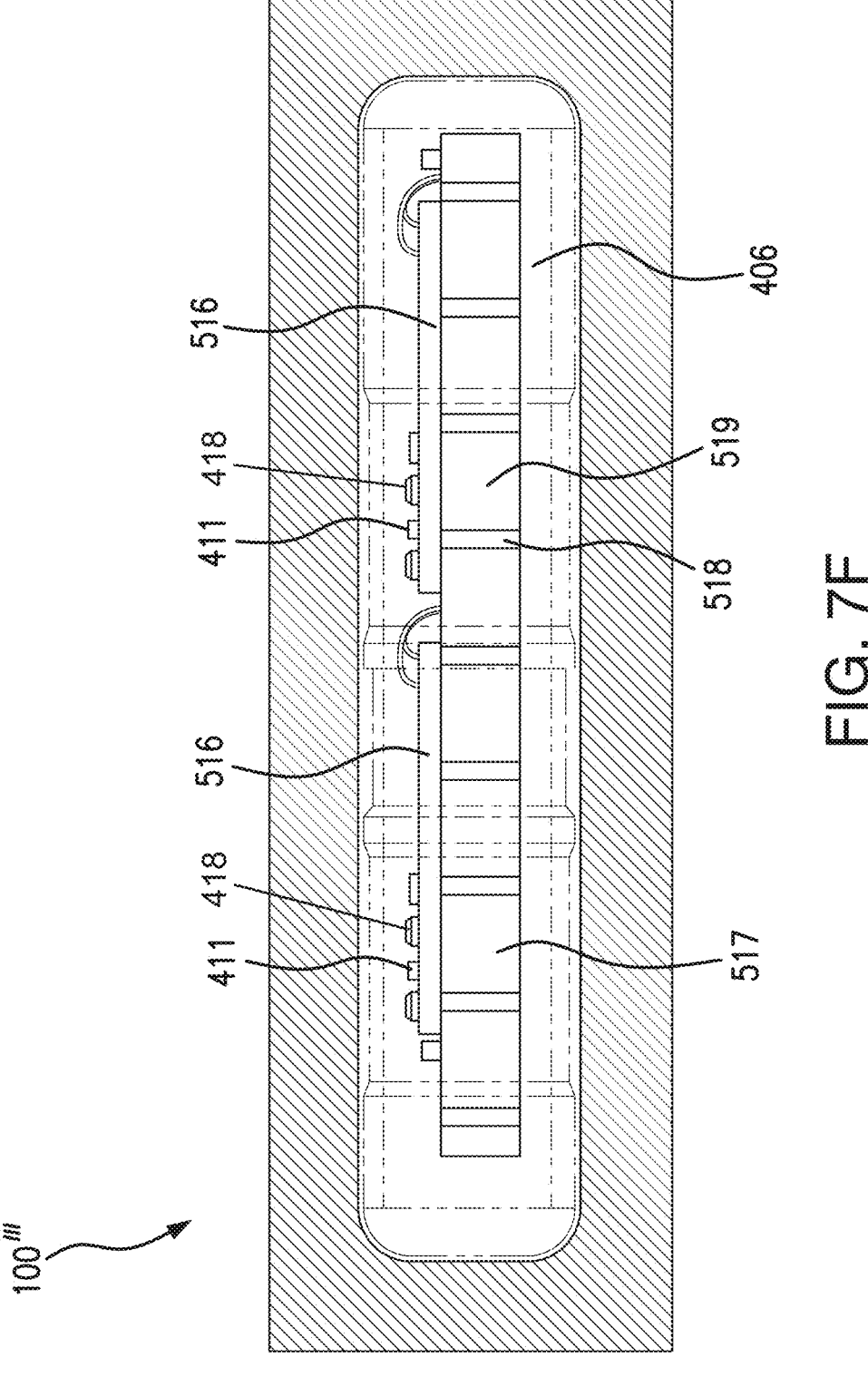

FIGS. 7A-7C are perspective, side, and cross-sectional views, respectively, of an analyte sensor 100" that is a second non-limiting example of the analyte sensor 100 of the analyte monitoring system 50. FIGS. 7D, 7E, and 7F are perspective and side views, respectively, of an analyte sensor 100'" that is a third non-limiting example of the analyte sensor 100 of the analyte monitoring system 50. In some embodiments, as shown in FIGS. 7A-7F, the analyte sensor 100 may include more than one substrate 516. In some embodiments, as shown in FIG. 7D, the analyte sensor 100 may include two or more indicator structures 409. In some embodiments, as shown in FIGS. 7E and 7F, the analyte sensor 100 may include a substrate 516 for each of the two or more indicator structures 409.

In some embodiments, as shown in FIGS. 7A-7C, the analyte sensor 100 may include one substrate 516 on one side of an inductor 517 and another substrate 516 on an opposite side of the inductor 517. Also, in some embodiments, as shown in FIGS. 7A-7C, the analyte sensor 100 may additionally or alternatively have one or more circuit components 722 (e.g., capacitors) mounted to the inductor 517.

In some alternative embodiments, as shown in FIGS. 7D-7F, the implantable device 100 may include two or more substrates 516 on one side of an inductor 517. In some non-limiting embodiments, as shown in FIG. 7E, one or more analyte photodetectors 415, one or more first interferent photodetectors 407a, and/or one or more second interferent photodetectors 407b may be mounted on or fabricated in each of the two or more substrates 516. However, this is not required, and, in some alternative embodiments, the one or more analyte photodetectors 415 may be mounted on or fabricated in only one of the substrates 516, and the one or more first interferent photodetectors 407a and/or one or more second interferent photodetectors 407b may be mounted on or fabricated in only another one of the substrates 516.

Figure 7G:
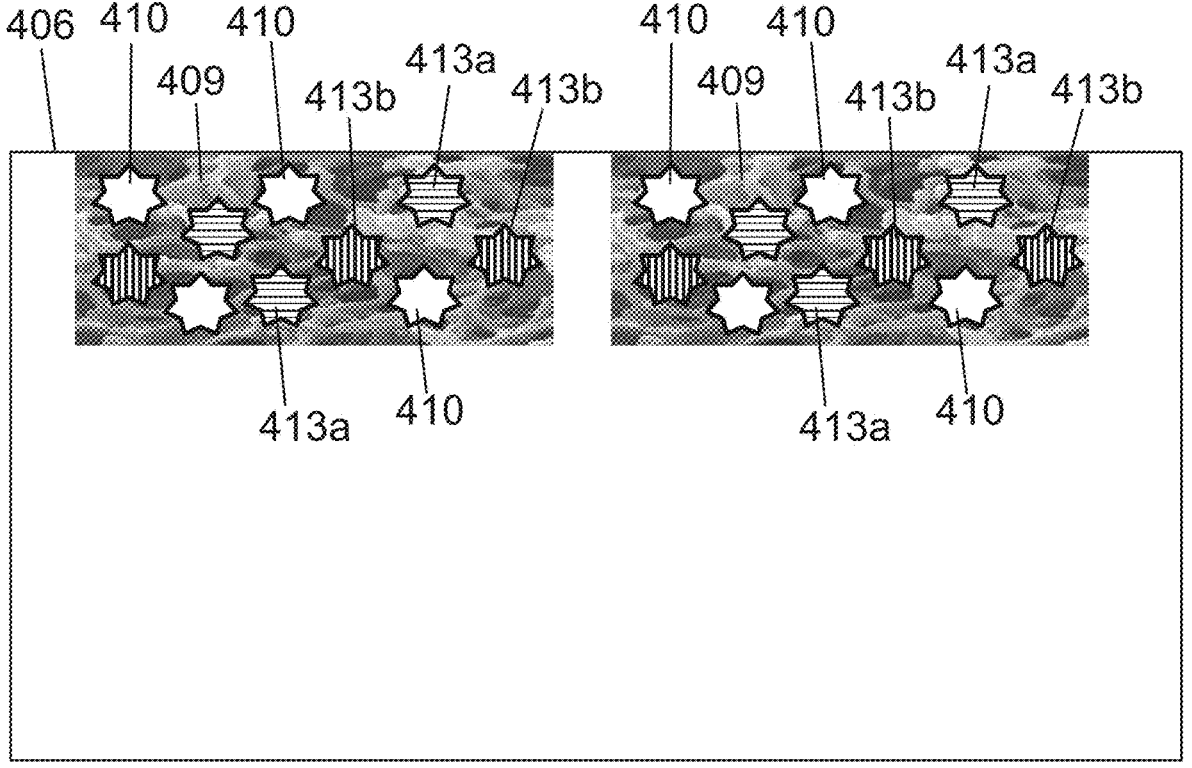

FIGS. 7G-7I illustrate non-limiting examples of the indicator structures 409 of an analyte sensor 100 including two or more indicator structures 409. In some embodiments in which the analyte sensor 100 includes two or more indicator structures 409 (e.g., analyte sensor 100'"), each of the two or more indicator structures 409 may be the same. For example, as shown in FIG. 7G, each of the two or more indicator structures 409 may include one or more of an analyte indicator 410, a first interferent indicator 413a, and a second interferent indicator 413b. In some alternative embodiments, in which the analyte sensor 100 includes two or more indicator structures 409 (e.g., analyte sensor 100'"), two or more of the indicator structures 409 may be different.

For example, as shown in FIG. 7H, one indicator structure 409a may include an analyte indicator 410, and another indicator structure 409b may include one or more of a first interferent indicator 413a and a second interferent indicator 413b. For another example, as shown in FIG. 7I, a first indicator structure 409a may include an analyte indicator 410 (and may not include any interferent indicators 413), a second indicator structure 409b may include a first interferent indicator 413a (and may include neither an analyte indicator 410 nor a second interferent indicator 413b), and a third indicator structure 409c may include a second interferent indicator 413b (and may include neither an analyte indicator 410 nor a first interferent indicator 413a).

In some embodiments, one or more of the indicator structures 409, light source(s) 411 and 418, photodetectors 407a, 407b, 415, circuit components, and substrates 516 of the analyte sensor 100 may include some or all of the features described in one or more of U.S. application Ser. No. 15/709,679, filed on Sep. 20, 2017, U.S. application Ser. No. 14/629,943, filed on Feb. 24, 2015, U.S. application Ser. No. 14/594,674, filed on Jan. 12, 2015, U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, and U.S. application Ser. No. 14/142,017, filed on Dec. 27, 2013, all of which are incorporated by reference in their entireties. Similarly, the structure, function, and/or features of the sensor housing 406, analyte sensor 100, and/or transceiver 101 may be as described in one or more of U.S. application Ser. Nos. 13/761,839, 13/937,871, 13/650,016, and 14/142,017. Although not shown in FIGS. 1B-7I, in some embodiments, the analyte sensor 100 (e.g., the circuit components of the analyte sensor 100) may include one or more temperature transducers capable of measuring temperature. Although in some aspects, as illustrated in FIGS. 1B-7I, the analyte sensor 100 may be an optical sensor, this is not required, and, in one or more alternative aspects, sensor 100 may be a different type of analyte sensor, such as, for example, an electrochemical sensor, a diffusion sensor, or a pressure sensor.

In some alternative embodiments, instead of (or in addition to) the one or more interferent detectors being configured to detect a detectable property of the one or more interferent indicators 413, the one or more interferent detectors (e.g., the one or more first interferent photodetectors 418a and/or the one or more second interferent photodetectors 418b) configured to output an interferent signal indicative of the amount or concentration of the interferent in the medium within the living animal may be absorption or reflectance sensors. For example, insulin has an absorption peak, and the one or more interferent sensor may measure the extent to which the interstitial fluid absorbs one or more wavelengths of light. In some non-limiting embodiments in which the one or more interferent detectors include absorption or reflectance sensors, the analyte sensor 100 may not include the one or more interferent indicators 413.

Figure 8:
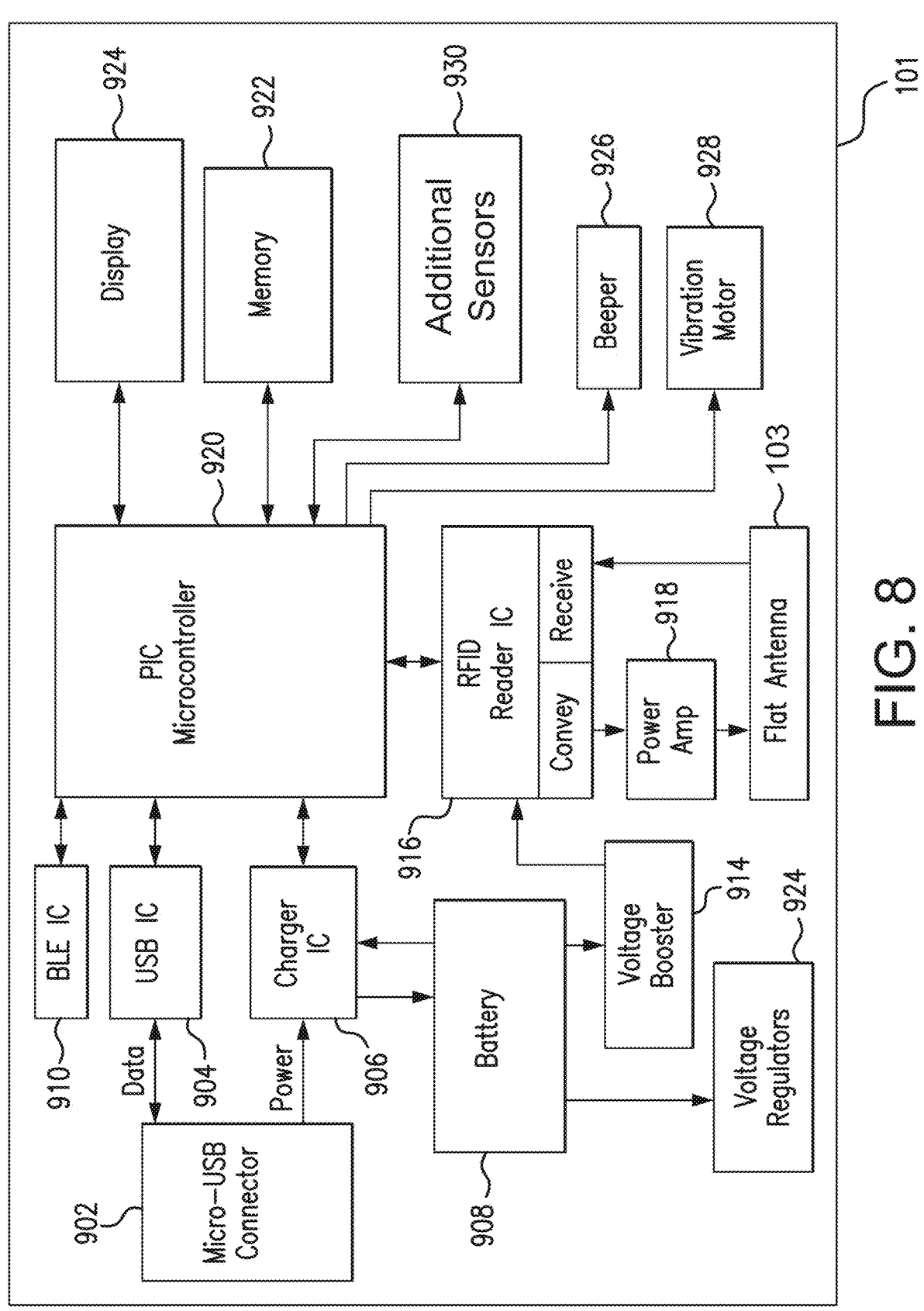
FIG. 8 is a schematic view illustrating a transceiver embodying aspects of the present invention.

FIG. 8 is a schematic view of an external transceiver 101 according to a non-limiting embodiment. In some aspects, as shown in FIG. 8, the transceiver 101 may have a connector 902, such as, for example, a Micro-Universal Serial Bus (USB) connector. The connector 902 may enable a wired connection to an external device, such as a personal computer or a display device 107 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some aspects, the battery 908 may be rechargeable, may have a short recharge duration, and/or may have a small size.

In some aspects, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer or a display device 107 (e.g., a smartphone) and/or to receive power, which may be used, for example, to charge the battery 908.

In some aspects, as shown in FIG. 8, the transceiver 101 may have a wireless communication IC 910, which enables wireless communication with an external device, such as, for example, one or more personal computers or one or more display devices 107 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting aspects, the wireless communication IC 910 may be configured to wirelessly transmit data at a frequency greater than 1 gigahertz (e.g., 2.4 or 5 GHz). In some aspects, the wireless communication IC 910 may include an antenna (e.g., a Bluetooth antenna). In some non-limiting aspects, the antenna of the wireless communication IC 910 may be entirely contained within the housing (e.g., housing 206 and 220) of the transceiver 101. However, this is not required, and, in alternative aspects, all or a portion of the antenna of the wireless communication IC 910 may be external to the transceiver housing.

In some aspects, the transceiver 101 may include a display interface, which may enable communication by the transceiver 101 with one or more display devices 107. In some aspects, the display interface may include the antenna of the wireless communication IC 910 and/or the connector 902. In some non-limiting aspects, the display interface may additionally include the wireless communication IC 910 and/or the connector IC 904.

In some aspects, as shown in FIG. 8, the transceiver 101 may include voltage regulators 912 and/or a voltage booster 914. The battery 908 may supply power (via voltage booster 914) to radio-frequency identification (RFID) reader IC 916, which uses the inductor 103 to convey information (e.g., commands) to the sensor 101 and receive information (e.g., measurement information) from the sensor 100. In some non-limiting aspects, the sensor 100 and transceiver 101 may communicate using near field communication (NFC) (e.g., at a frequency of 13.56 MHz). In the illustrated embodiment, the inductor 103 is a flat antenna. In some non-limiting aspects, the antenna may be flexible. However, the inductor 103 of the transceiver 101 may be in any configuration that permits adequate field strength to be achieved when brought within adequate physical proximity to the inductor 114 of the sensor 100. In some aspects, the transceiver 101 may include a power amplifier 918 to amplify the signal to be conveyed by the inductor 103 to the sensor 100.

In some aspects, as shown in FIG. 8, the transceiver 101 may include a processor 920 and a memory 922 (e.g., Flash memory). In some non-limiting aspects, the memory 922 may be non-volatile and/or capable of being electronically erased and/or rewritten. In some non-limiting aspects, the processor 920 may be, for example and without limitation, a peripheral interface controller (PIC) microcontroller. In some aspects, the processor 920 may control the overall operation of the transceiver 101. For example, the processor 920 may control the connector IC 904 or wireless communication IC 910 to transmit data via wired or wireless communication and/or control the RFID reader IC 916 to convey data via the inductor 103. The processor 920 may also control processing of data received via one or more of the inductor 103, connector 902, and wireless communication IC 910.

In some aspects, the transceiver 101 may include a sensor interface, which may enable communication by the transceiver 101 with an analyte sensor 100. In some aspects, the sensor interface may include the inductor 103. In some non-limiting aspects, the sensor interface may additionally include the RFID reader IC 916 and/or the power amplifier 918. However, in some alternative aspects where there exists a wired connection between the analyte sensor 100 and the transceiver 101 (e.g., transcutaneous aspects), the sensor interface may include the wired connection.

In some aspects, as shown in FIG. 8, the transceiver 101 may include a display 924 (e.g., liquid crystal display and/or one or more light emitting diodes), which processor 920 may control to display data (e.g., analyte levels). In some aspects, the transceiver 101 may include a speaker 926 (e.g., a beeper) and/or a vibration motor 928, which may be activated, for example, in the event that an alarm condition (e.g., detection of a hypoglycemic or hyperglycemic condition) is met. The transceiver 101 may also include one or more additional sensors 930, which may include an accelerometer, temperature sensor, and/or one or more interferent sensors, that may be used in the processing performed by the processor 920. In some non-limiting embodiments in which the one or more additional sensors 930 of the transceiver 101 include one or more interferent sensors, the one or more interferent sensors may generate one or more interferent measurements indicative of a level of one or more interferents (e.g., a first interferent and/or a second interferent) in the first medium (e.g., interstitial fluid). In some non-limiting embodiments in which the one or more additional sensors 930 include one or more interferent sensors, the one or more interferent sensors may be include absorption or reflectance sensors. For example, insulin has an absorption peak, and the one or more interferent sensors may measure the extent to which the interstitial fluid absorbs one or more wavelengths of light. In some non-limiting embodiments in which the one or more additional sensors 930 include one or more interferent sensors, the interferent measurements generated by the one or more interferent sensors of the additional sensors 930 may be in addition, or as an alternative, to interferent measurements generated by the analyte sensor 100.

In some aspects, the transceiver 101 may be a body-worn transceiver that is a rechargeable, external device worn over the sensor implantation or insertion site. In some aspects, the transceiver 101 may be placed using an adhesive patch or a specially designed strap or belt. In some non-limiting aspects, the transceiver 101 may supply power to the proximate sensor 100. In some non-limiting aspects, power may be supplied to the sensor 100 through an inductive link (e.g., an inductive link of 13.56 MHz). However, it is not required that the sensor 100 receive power from the transceiver 101 (e.g., in the case of a battery-powered sensor).

In some embodiments, the transceiver 101 of the analyte monitoring system 50 may receive one or more sensor measurements indicative of an amount, level, or concentration of an analyte in a first medium (e.g., interstitial fluid (ISF)) in proximity to the analyte sensor 100. In some non-limiting embodiments, the one or more sensor measurements may include, for example and without limitation, light and/or temperature measurements (e.g., one or more measurements indicative of the level of analyte emission light 414 from one or more analyte indicators 410 as measured by one or more analyte photodetectors 415, one or more measurements indicative of the level of first interferent emission light from one or more first interferent indicators 413a as measured by one or more first interferent photodetectors 407a, one or more measurements indicative of the level of second interferent emission light from one or more second interferent indicators 413b as measured by one or more second interferent photodetectors 407b, and/or one or more temperature measurements as measured by one or more temperature transducers). In some embodiments, the transceiver 101 may receive the sensor measurements from the analyte sensor 100 periodically (e.g., every 1, 2, 5, 10, 15, or 20 minutes). However, this is not required, and, in some alternative aspects, the transceiver 101 may receive one or more sensor measurements (e.g., by swiping, hovering, or otherwise bringing the transceiver 101 in proximity to the sensor 101).

In some embodiments, the transceiver 101 may use the received sensor measurements to calculate a first medium analyte level (e.g., an ISF analyte level). In some embodiments, the transceiver 101 may use the calculated first medium analyte level and at least one or more previously calculated first medium analyte levels to calculate a rate of change of the first medium analyte level ("M1_ROC"). In some non-limiting embodiments, to calculate M1_ROC, the transceiver 101 may use just the calculated first medium analyte level and the most recent previously calculated first medium analyte level and determine M1_ROC as the difference between the calculated first medium analyte level and most recent previously calculated first medium analyte level divided by the time difference between a time stamp for the calculated first medium analyte level and a time stamp for the most recent previously calculated first medium analyte level. In some alternative embodiments, to calculate M1_ROC, the transceiver 101 may use the calculated first medium analyte level and a plurality of the most recent previously calculated first medium analyte levels. In some non-limiting embodiments, the plurality of the most recent previously calculated ISF analyte levels may be, for example and without limitation, the previous two calculated first medium analyte levels, the previous 20 calculated first medium analyte levels, or any number of previously calculated ISF analyte levels in between (e.g., the previous 5 calculated first medium analyte levels). In other alternative embodiments, to calculate M1_ROC, the transceiver 101 may use the calculated first medium analyte level and the previously calculated first medium analyte levels that were calculated during a time period. In some non-limiting embodiments, the time period may be, for example and without limitation, the last one minute, the last 60 minutes, or any amount of time in between (e.g., the last 25 minutes). In some embodiments where the transceiver 101 uses the calculated first medium analyte level and more than one previously calculated first medium analyte levels to calculate M1_ROC, the transceiver 101 may use, for example, linear or non-linear regression to calculate M1_ROC.

In some embodiments, the transceiver 101 may convert the calculated first medium analyte level into a second medium analyte level (e.g., a blood analyte level) by performing a lag compensation, which compensates for the lag between a second medium analyte level and an first medium analyte level (e.g., the lag between a blood analyte level and an ISF analyte level). In some embodiments, the transceiver 101 may calculate the second medium analyte level using at least the calculated first medium analyte level and the calculated M1_ROC. In some non-limiting embodiments, the transceiver 101 may calculate the second medium analyte level as $M1\_ROC/p_2+(1+p_3/p_2)*M1\_analyte$, where $p_2$ is analyte diffusion rate, $p_3$ is the analyte consumption rate, and M1_analyte is the calculated first medium analyte level.

In some embodiments, one or more interferents (e.g., insulin and blood) in the first medium (e.g., ISF) may affect the lag between the second medium analyte level and the first medium analyte level. For example and without limitation, one or more interferents in the first medium may affect the transfer of the analyte from the second medium (e.g., blood) to the first medium (e.g., interstitial fluid) in proximity to the sensor 100. In some embodiments, the analyte monitoring system 50 may use one or more interferent measurements indicative of the amount or concentration of one or more interferents in the first medium to improve the calculation of second medium analyte levels. In some non-limiting embodiments, the analyte monitoring system 50 may use one or more interferent measurements indicative of the amount or concentration of one or more interferents in the first medium to improve the conversion of a first medium analyte level to second medium analyte level.

In some embodiments, the transceiver 101 may use one or more analyte measurements (e.g., generated using the analyte signal output by the one or more analyte photodetectors 415) and one or more interferent measurements (e.g., one or more first interferent measurements generated using the first interferent signal output by the one or more first interferent photodetectors 407a and/or one or more second interferent measurements generated using the second interferent signal output by the one or more second interferent photodetectors 407b) received from the analyte sensor 100 to calculate a second medium analyte level. In some non-limiting embodiments, the transceiver 101 may adjust a conversion function used to calculate a second medium analyte level based on one or more interferent measurements. In some non-limiting embodiments, the transceiver 101 may adjust the conversion function by adjusting one or more parameters (e.g., one or more of the analyte diffusion rate and analyte consumption rate parameters) of the conversion function. In some non-limiting embodiments, the transceiver 101 may adjust one or more of $p_2$ and $p_3$ (or one or more of $1/p_2$ and $p_3/p_2$) in the conversion function that calculates a second medium analyte level as $M1\_ROC/p_2+(1+p_3/p_2)*M1\_analyte$. In some alternative embodiments, the transceiver 101 may select one of a plurality of conversion functions based on one or more interferent measurements.

In some embodiments, the transceiver 101 may calculate the second medium analyte level (e.g., blood analyte level) using at least one or more analyte measurements and one or more interferent measurements received from the analyte sensor 100. In some non-limiting embodiments, the transceiver 101 may calculate one or more interferent levels in the first medium using at least the one or more interferent measurements. In some non-limiting embodiments, interferent measurements may include one or more first interferent measurements and one or more second interferent measurements, and the transceiver 101 may calculate a first interferent level in the first medium using at least the one or more first interferent measurements and a second interferent level in the first medium using at least the one or more second interferent measurements. In some non-limiting embodiments, the transceiver 101 may calculate the second medium analyte level using at least one or more analyte measurements and the one or more calculated interferent levels (e.g., one or more calculated first interferent levels and/or one or more calculated second interferent levels). In some non-limiting embodiments, the transceiver 101 may adjust one or more parameters of the conversion function (e.g., one or more of the analyte diffusion rate and the analyte consumption rate) based on at least the one or more calculated interferent levels and may use the adjusted conversion function and the one or more analyte measurements to calculate the second medium analyte level. In some non-limiting alternative embodiments, the transceiver 101 may select one of a plurality of conversion functions based on the one or more calculated interferent levels and use the selected conversion function and the one or more analyte measurements to calculate the second medium analyte level.

In some non-limiting embodiments, the transceiver 101 may additionally or alternatively adjust one or more analyte measurements or temperature measurements received from the analyte sensor 100 using one or more of the interferent measurements. For example and without limitation, one or more of the interferents may interfere with the ability of the analyte to bind with the analyte sensor 410. Accordingly, the one or more analyte measurements may be different than they would be if the one or more interferents were not present in the first medium (or if different levels of the one or more interferents were present in the first medium). In some embodiments, the transceiver 101 may, for example and without limitation, adjust (e.g., increase) one or more analyte measurements. In some embodiments, the transceiver 101 may use one or more adjusted analyte measurements (instead of the original analte measurements from the analyte sensor 100) to calculate the second medium analyte level (e.g., the blood analyte level). In some non-limiting embodiments, the transceiver 101 may use one or more adjusted analyte measurements (instead of the original analyte measurements from the analyte sensor 100) to calculate the first medium analyte level (e.g., the ISF analyte level), which may be used to calculate the second medium analyte level.

In some aspects, the transceiver 101 may display one or more calculated analyte levels (e.g., one or calculated second medium analyte levels) by displaying the analyte levels on a display of the transceiver 101 or conveying the analyte levels to a display device 107 (see FIG. 1). In some aspects, the transceiver 101 may determine whether an alert and/or alarm condition exists, which may be signaled to the user (e.g., through vibration by vibration motor 928, an LED of the transceiver's display 924, and/or a user interface of a display device 107). In some aspects, the transceiver 101 may store one or more calculated analyte levels and/or one or more calculated interferent levels (e.g., in memory 922).

In some aspects, the transceiver 101 may convey information (e.g., one or more of sensor data, calculated analyte levels, calculated analyte level rates of change, calculated interferent levels, alerts, alarms, and notifications) may be transmitted to a display device 107 (e.g., via Bluetooth Low Energy with Advanced Encryption Standard (AES)-Counter CBC-MAC (CCM) encryption) for display by a mobile medical application (MMA) being executed by the display device 107. In some non-limiting aspects, the MMA may generate alarms, alerts, and/or notifications (in addition to or as an alternative to receiving alerts, alarms, and/or notifications from the transceiver 101). In one embodiment, the MMA may be configured to provide push notifications.

In some aspects, the analyte monitoring system 50 may calibrate the conversion of one or more analyte measurements to one or more analyte levels. In some aspects, the calibration may be performed approximately periodically (e.g., every 12 or 24 hours). In some aspects, the calibration may be performed using one or more reference measurements (e.g., one or more self-monitoring blood glucose (SMBG) measurements), which may be entered into the analyte monitoring system 50 using the user interface of the display device 107. In some aspects, the transceiver 101 may receive the one or more reference measurements from the display device 107 and perform the calibration using the one or more reference measurements as calibration points.

Figure 9:
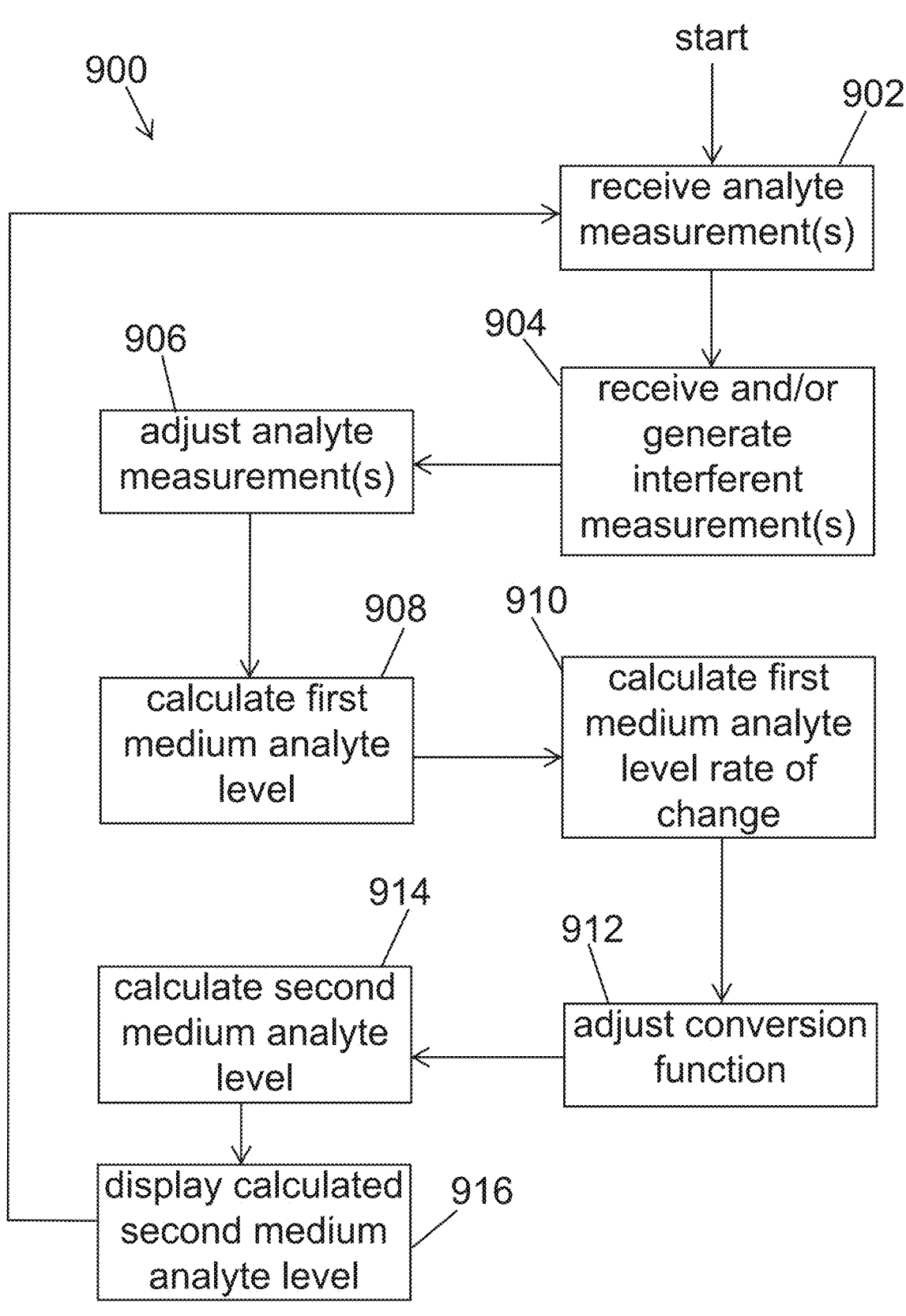
FIG. 9 is a flow chart illustrating an analyte level calculation process embodying aspects of the present invention.

FIG. 9 is a flow chart illustrating a process 900 for calculating second medium analyte levels (e.g., blood analyte levels). In some embodiments, one or more steps of the process 900 may be performed by an analyte monitoring system, such as, for example, the analyte monitoring system 50. In some embodiments, one or more steps of the process 900 may be performed by a transceiver, such as, for example, the transceiver 101. In some non-limiting embodiments, one or more steps of the process 900 may be performed by a processor, such as, for example, the processor 920 of the transceiver 101.

In some embodiments, the process 900 may include a step 902 in which the transceiver 101 receives one or more analyte measurements from the analyte sensor 100. In some non-limiting embodiments, the one or more analyte measurements may include, for example and without limitation, one or more light measurements (e.g., generated using the one or more analyte photodetectors 415). In some non-limiting embodiments, the analyte measurements may additionally include one or more temperature measurements. In some embodiments, the transceiver 101 may receive the one or more analyte measurements after conveying a command (e.g., a measurement command or a read sensor data command) to the analyte sensor 100. However, this is not required, and, in some alternative embodiments, the analyte sensor 100 may control when one or more analyte measurements are conveyed to the transceiver 101, or the analyte sensor 100 may continuously convey analyte measurements to the transceiver 101. In some non-limiting embodiments, the transceiver 101 may receive one or more analyte measurements periodically (e.g., every 1, 2, 5, 10, or 15 minutes).

In some embodiments, the transceiver 101 may receive the one or more analyte measurements using the sensor interface (e.g., one or more of the inductor 103, RFID reader IC 916, and the power amplifier 918) of the transceiver 101. In some non-limiting embodiments, the transceiver 101 may receive the one or more analyte measurements wirelessly. For example and without limitation, in some non-limiting embodiments, the transceiver 101 may receive the one or more analyte measurements by detecting modulations in an electromagnetic wave generated by the sensor 100, e.g., by detecting modulations in the current flowing through the inductor 103 of the transceiver 101. However, this is not required, and, in some alternative embodiments, the transceiver 101 may receive the one or more analyte measurements via a wired connection to the sensor 100.

In some embodiments, the one or more analyte measurements may be associated with a time stamp. In some non-limiting embodiments, the transceiver 101 may receive the time stamp from the sensor 100. In some non-limiting embodiments, the received one or more analyte measurements may include the time stamp. In some embodiments, the time stamp may reflect the time at which the one or more analyte measurements were taken. However, it is not required that the transceiver 101 receive the time stamp from the sensor 100. For example, in some alternative embodiments, the transceiver 101 may assign the time stamp to the one or more analyte measurements after receiving the one or more analyte measurements. In these embodiments, the time stamp may reflect when the transceiver 101 received the one or more analyte measurements.

In some embodiments, the process 900 may include a step 904 in which the transceiver 101 receives or generates one or more interferent measurements. In some embodiments, the one or more interferent measurements may include one or more first interferent measurements indicative of a level of a first interferent in the first medium and/or one or more second interferent measurements indicative of a level of a second interferent in the first medium. In some non-limiting embodiments, the one or more interferent detectors (e.g., the one or more of the interferent photodetectors 407) of the analyte sensor 100 generate the one or more interferent measurements received from the analyte sensor 100. In some non-limiting embodiments, the transceiver 101 may additionally or alternatively generate one or more interferent measurements using one or more interferent sensors of the additional sensors 930 of the transceiver 101.

In some embodiments, the process 900 may include a step 906 in which the transceiver 101 adjusts one or more analyte measurements received from the sensor 100. In some embodiments, the transceiver 101 may adjust one or more analyte measurements based on one or more interferent measurements.

In some embodiments, the process 900 may include a step 908 in which the transceiver 101 calculates first medium analyte level (e.g., an ISF analyte level) using the one or more analyte measurements received from the analyte sensor 100. In some embodiments, one or more of the analyte measurements used to calculate the first medium analyte level may have been adjusted in step 906. In some embodiments, the first medium analyte level may be a measurement of the amount or concentration of the analyte in the first medium (e.g., interstitial fluid) in proximity to the analyte sensor 100. In some non-limiting embodiments, calculation of the first medium analyte level may include, for example and without limitation, some or all of the features described in U.S. application Ser. No. 13/937,871, filed on Jul. 9, 2013, now U.S. Pat. No. 9,414,775, which is incorporated by reference herein in its entirety.

In some embodiments, the process 900 may include a step 910 in which the transceiver 101 calculates a first medium analyte level rate of change ("M1_ROC"). In some embodiments, the transceiver 101 may calculate the M1_ROC using at least the first medium analyte level calculated in step 908 and one or more previously calculated first medium analyte levels (e.g., one or more first medium analyte levels calculated using previously received sensor measurements).

In some embodiments, the process 900 may include a step 912 in which the transceiver 101 adjusts a conversion function used to calculate a second medium analyte level (e.g., a blood analyte level) based on one or more interferent measurements. In some non-limiting embodiments, the transceiver 101 may adjust the conversion function by adjusting one or more parameters (e.g., one or more of the analyte diffusion rate and analyte consumption rate parameters) of the conversion function. In some alternative embodiments, in step 912, the transceiver 101 may select one of a plurality of conversion functions based on one or more interferent measurements (e.g., one or more interferent measurements generated by the one or more intereferent detectors of the analyte sensor 100).

In some embodiments, the process 900 may include a step 914 in which the transceiver 101 calculates a second medium analyte level (e.g., a blood analyte level). In some embodiments, the transceiver 101 may calculate the second medium analyte level by performing a lag compensation. In some embodiments, the transceiver 101 may calculate the second medium analyte level using at least the first medium analyte level and the M1_ROC calculated in steps 908 and 910, respectively. In some embodiments, the transceiver 101 may calculate the second medium analyte level using a conversion function. In some non-limiting embodiments, the conversion function used in step 914 may have been adjusted (or selected) in step 912.

In some non-limiting embodiments, the process 900 may include a step 916 of displaying the calculated second medium analyte level. In some embodiments, the step 916 may include displaying the calculated second medium analyte level on a display of the transceiver 101. In some embodiments, the step 916 may additionally or alternatively include the transceiver 101 conveying the calculated second medium analyte level to a display device (e.g., display device 107) for display. In some non-limiting embodiments, the transceiver 101 may convey the calculated second medium analyte level to the display device 107 via wired or wireless communication using the display interface (e.g., one or more of the antenna of the wireless communication IC 910, the connector 902, the wireless communication IC 910, and the connector IC 904). In some embodiments, the display device 107 may be configured to receive and display the conveyed second medium analyte level.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although the invention is described above in the context of an analyte monitoring system that calculates blood analyte levels indirectly using measurements of analyte levels in interstitial fluid, the invention is applicable to any monitoring system that calculates levels in a first medium using measurements of levels in a second medium.

What is claimed is:

1. An analyte monitoring system comprising:
an analyte sensor comprising:
   an indicator structure;
   analyte indicator molecules configured to reversibly bind an analyte in a first medium and, in response to being irradiated with analyte excitation light, emit analyte emission light indicative of whether the analyte is bound and therefore indicative of a level of the analyte in the first medium, wherein the analyte indicator molecules are distributed throughout the indicator structure;
   interferent indicator molecules configured to reversibly bind an interferent in the first medium and, in response to being irradiated with interferent excitation light, emit interferent emission light indicative of whether the interferent is bound and therefore indicative of a level of the interferent in the first medium, wherein the interferent indicator molecules are distributed throughout the indicator structure, and the interferent indicator molecules are different than the analyte indicator molecules;
an analyte photodetector configured to output an analyte signal indicative of an amount of the analyte emission light received by the analyte photodetector,
an interferent photodetector configured to output an interferent signal indicative of an amount of the interferent emission light received by the interferent photodetector, and
a transceiver interface configured to convey an analyte measurement and an interferent measurement, wherein the analyte measurement is a measurement of the analyte signal, and the interferent measurement is a measurement of the interferent signal; and
a transceiver comprising: (i) a sensor interface configured to receive the analyte and interferent measurements conveyed by the transceiver interface of the analyte sensor and (ii) a processor configured to calculate an analyte level in a second medium using at least the analyte and interferent measurements.

2. The analyte monitoring system of claim 1, wherein calculating the analyte level in the second medium comprises:
   calculating an analyte level in the first medium using at least the analyte measurement;
   calculating an interferent level in the first medium using at least the interferent measurement; and
   calculating the analyte level in the second medium using at least the calculated analyte level in the first medium and the calculated interferent level in the first medium.

3. The analyte monitoring system of claim 2, wherein calculating the analyte level in the second medium using at least the calculated analyte level in the first medium and the calculated interferent level in the first medium comprises:
   adjusting one or more parameters of a conversion function based on at least the calculated interferent level in the first medium; and
   using at least the adjusted conversion function and the calculated analyte level in the first medium to calculate the analyte level in the second medium.

4. The analyte monitoring system of claim 1, wherein the analyte sensor further comprises an analyte excitation light source configured to irradiate the analyte indicator molecules with the analyte excitation light.

5. The analyte monitoring system of claim 4, wherein the analyte excitation light source is further configured to irradiate the interferent indicator molecules with the interferent excitation light, and the analyte excitation light and the interferent excitation light are the same light.

6. The analyte monitoring system of claim 4, wherein the analyte sensor further comprises an interferent excitation light source configured to irradiate the interferent indicator molecules with the interferent excitation light, and a wavelength range of the analyte excitation light is different than a wavelength range of the interferent excitation light.

7. The analyte monitoring system of claim 1, wherein:
   the interferent indicator molecules are first indicator molecules,
   the interferent emission light is first interferent emission light,
   the interferent is a first interferent,
   the interferent photodetector is a first interferent photodetector,
   the interferent signal is a first interferent signal, the interferent measurement is a first interferent measurement, and the analyte sensor further comprises:

second interferent indicator molecules configured to emit second interferent emission light indicative of a level of a second interferent in the first medium; and a second interferent photodetector configured to output a second interferent signal indicative of an amount of the second interferent emission light received by the second interferent photodetector, the transceiver interface is further configured to convey a second interferent measurement that is a measurement of the second interferent signal, the sensor interface is further configured to receive the second interferent measurement conveyed by the transceiver interface of the analyte sensor, and the processor is configured to calculate the analyte level in the second medium using at least the analyte measurement, the first interferent measurement, and the second interferent measurement.

8. The analyte monitoring system of claim 7, wherein the first medium is interstitial fluid, the second medium is blood, the analyte is glucose, the first interferent is insulin, and the second interferent is blood.

9. The analyte monitoring system of claim 1, wherein first medium is interstitial fluid, the second medium is blood, the analyte is glucose, and the interferent is insulin or blood.

10. The analyte monitoring system of claim 1, wherein the indicator structure is a single, unitary structure.

11. A method performed by an analyte monitoring system, the method comprising:

using analyte indicator molecules of an analyte sensor of the analyte monitoring system to reversibly bind an analyte in a first medium, wherein the analyte indicator molecules are distributed throughout an indicator structure of the analyte sensor;

using interferent indicator molecules of the analyte sensor to reversibly bind an interferent in the first medium, wherein the interferent indicator molecules are distributed throughout the indicator structure, and the interferent indicator molecules are different than the analyte indicator molecules;

using the analyte indicator molecules to emit analyte emission light indicative of whether the analyte is bound and therefore indicative of a level of the analyte in the first medium in response to being irradiated with analyte excitation light;

using the interferent indicator molecules to emit interferent emission light indicative of whether the interferent is bound and therefore indicative of a level of the interferent in the first medium in response to being irradiated with interferent excitation light;

using an analyte photodetector of the analyte sensor to output an analyte signal indicative of an amount of the analyte emission light received by the analyte photodetector;

using an interferent photodetector of the analyte sensor to output an interferent signal indicative of an amount of the interferent emission light received by the interferent photodetector;

using a transceiver interface of the analyte sensor to convey an analyte measurement and an interferent measurement, wherein the analyte measurement is a measurement of the analyte signal, and the interferent measurement is a measurement of the interferent signal;

using a sensor interface of a transceiver of the analyte monitoring system to receive the analyte and interferent measurements conveyed by the transceiver interface of the analyte sensor;

using a processor of the transceiver to calculate an analyte level in a second medium using at least the analyte and interferent measurements.

12. The method of claim 11, wherein calculating the analyte level in the second medium comprises:

calculating an analyte level in the first medium using at least the analyte measurement;

calculating an interferent level in the first medium using at least the interferent measurement; and calculating the analyte level in the second medium using at least the calculated analyte level in the first medium and the calculated interferent level in the first medium.

13. The method of claim 12, wherein calculating the analyte level in the second medium using at least the calculated analyte level in the first medium and the calculated interferent level in the first medium comprises:

adjusting one or more parameters of a conversion function based on at least the calculated interferent level in the first medium; and using at least the adjusted conversion function and the calculated analyte level in the first medium to calculate the analyte level in the second medium.

14. The method of claim 11, further comprising:

using an analyte excitation light source of the analyte sensor to irradiate the analyte indicator molecules of the analyte sensor with the analyte excitation light.

15. The method of claim 14, further comprising:

using the analyte excitation light source to irradiate the interferent indicator molecules of the analyte sensor with the interferent excitation light, and the analyte excitation light and the interferent excitation light are the same light.

16. The method of claim 14, further comprising:

using an interferent excitation light source of the analyte sensor to irradiate the interferent indicator molecules of the analyte sensor with the interferent excitation light, wherein a wavelength range of the analyte excitation light is different than a wavelength range of the interferent excitation light.

17. The method of claim 11, wherein:

the interferent indicator molecules are first indicator molecules, the interferent emission light is first interferent emission light, the interferent is a first interferent, the interferent photodetector is a first interferent photodetector, the interferent signal is a first interferent signal, the interferent measurement is a first interferent measurement, and the method further comprises:

using second interferent indicator molecules of the analyte sensor to emit second interferent emission light indicative of a level of a second interferent in the first medium; and using a second interferent photodetector of the analyte sensor to output a second interferent signal indicative of an amount of the second interferent emission light received by the second interferent photodetector;

using the transceiver interface of the analyte sensor to convey a second interferent measurement that is a measurement of the second interferent signal; and using the sensor interface of the transceiver to receive the second interferent measurement conveyed by the transceiver interface of the analyte sensor;

using the processor of the transceiver to calculate the analyte level in the second medium using at least the analyte measurement, the first interferent measurement, and the second interferent measurement.

18. The method of claim 17, wherein the first medium is interstitial fluid, the second medium is blood, the analyte is glucose, the first interferent is insulin, and the second interferent is blood.

19. The method of claim 11, wherein the first medium is interstitial fluid, the second medium is blood, the analyte is glucose, and the interferent is insulin or blood.

20. The method of claim 11, wherein the indicator structure is a single, unitary structure.

* * * * *